US005310671A

United States Patent [19]

Binns et al.

[11] Patent Number: 5,310,671

[45] Date of Patent: May 10, 1994

[54] FOWLPOX VIRUS NON-ESSENTIAL REGIONS

[75] Inventors: Matthew M. Binns; Michael E. G. Boursnell; Joan I. A. Campbell, all of Huntingdon; Fiona M. Tomley, Cambridge, all of England

[73] Assignee: British Technology Group Limited, London, England

[21] Appl. No.: 613,565

[22] PCT Filed: Jun. 22, 1989

[86] PCT No.: PCT/GB89/00698

§ 371 Date: Nov. 28, 1990

§ 102(e) Date: Nov. 28, 1990

[87] PCT Pub. No.: WO89/12684

PCT Pub. Date: Dec. 28, 1989

[30] Foreign Application Priority Data

| | | | |
|---|---|---|---|
| Jun. 24, 1988 | [GB] | United Kingdom | 815098 |
| Feb. 27, 1989 | [GB] | United Kingdom | 8904411 |
| Mar. 31, 1989 | [GB] | United Kingdom | 8907374 |
| May 8, 1989 | [GB] | United Kingdom | 8910520 |

[51] Int. Cl.[5] .......................... C12N 7/01; C12N 15/39; C12N 15/86; C12N 5/10

[52] U.S. Cl. .......................... 435/235.1; 435/320.1; 435/240.2; 536/23.72; 536/24.2; 535/32

[58] Field of Search ............... 435/320.1, 235.1, 172.3, 435/240.2; 424/89, 93; 536/27, 23.1, 23.73, 24; 935/32, 57, 65

[56] References Cited

U.S. PATENT DOCUMENTS

| | | | |
|---|---|---|---|
| 5,093,258 | 3/1992 | Cohen et al. | 435/235.1 |
| 5,174,993 | 12/1992 | Paoletti | 424/89 |

FOREIGN PATENT DOCUMENTS

| | | | |
|---|---|---|---|
| 0284416 | 9/1988 | European Pat. Off. | C12N 15/00 |
| 0308220 | 3/1989 | European Pat. Off. | C12N 15/00 |
| 0314569 | 5/1989 | European Pat. Off. | C12N 15/00 |
| WO86/00528 | 1/1986 | PCT Int'l Appl. | A61K 39/02 |
| 8802022 | 3/1988 | PCT Int'l Appl. | C12N 15/00 |
| WO89/03429 | 4/1989 | PCT Int'l Appl. | C12P 21/00 |
| 9002191 | 3/1990 | PCT Int'l Appl. | C12N 15/86 |

OTHER PUBLICATIONS

Jenkins, S. et al.. 1991, *AIDS Res. and Human Retrovir.* vol. 7 pp. 991-998.

Coupar, B. E. H. et al. 1990, *Virology* vol. 167 pp. 159-167.

Muller, H. K., et al. 1977 *J. Gen. Virol.* vol. 38 pp. 135-147.

Ghildyal, N. et al.. 1989 *Arch. Virol.* vol. 106 pp. 85-92.

Schnitzlein , W. M. et al. 1988 *Virus Res.* vol. 10 pp. 65-76.

Esposito, J. J. et al. 1989, *Adv. Vet. Sci and Compar. Med.* vol. 33 pp. 195-247.

Binns, M. M. et al. 1986, *Israeli J. Vet. Med.* vol. 4 pp. 124-127.

Drillien, R. et al. 1987, *Virology* vol. 160 pp. 203-209.

Mockett, B. et al. 1992, J. Gen. Virol. vol. 73 pp. 2661-2668.

Perkus, M. E. et al. 1985, *Science* vol. 229 pp. 981-984.

Taylor, J. et al, 1988, *Vaccine,* vol. 6, pp. 504-508.

B. Moss et al., Virology 40 387-395 (1981).

D. Panicali et al., J. Virol. 37 1000-1010 (1981).

(List continued on next page.)

*Primary Examiner*—Richard A. Schwartz

*Assistant Examiner*—May E. Mosher

*Attorney, Agent, or Firm*—Nixon & Vanderhye

[57] ABSTRACT

The invention relates to DNA from fowlpox virus (FPV) providing a non-essential region for the insertion of foreign genes thereinto and thence the construction of a vector for homologous recombination with a wild type FPV, whereby the resulting recombinant FPV can be used for vaccination of animals, especially chickens. In this invention, the non-essential region consists substantially of a length of DNA from the long unique sequence of the terminal inverted repeat (TIR) of FPV or from the region at FPV which corresponds approximately to the HindIII D fragment genes D8 and D9 in vaccinia virus.

10 Claims, 17 Drawing Sheets

OTHER PUBLICATIONS

D. B. Boyle et al., Virology 156 355-365 (1987).
M. Binns et al., Nucl. Acid. Res. 15 6563-6573 (1987).
F. M. Tomley Talk at 6th Workship on Poxvirus-/iridovirus, Cold Spring Harbour, N.Y., 24≧26 Sep. 1986.
F. M. Tomley et al., J. Gen. Virology 69 1025-1040 (1988).
M. Mackett et al., J. Gen. Virol. 45 683-701 (1979).
M. E. Perkus et al., Virol. 152 285-297 (1986).
J. I. A. Campbell Poster at International Poxvirus Workship, Cold Spring Harbour, N.Y., 9-13 Sep. 1987.
J. I. A. Campbell et al., J. Gen. Virol. 70 145-154 (1989).
S. Venkatesan et al., J. Virol. 44 637-646 (1982).
Niles et al., Virol. 153 96-112 (1986).
Seto et al., Virol. 160 110-110 (1987).
Niles & Seto J. Virol. 62 3772-3778 (1988)

| | |
|---|---|
| ▦ | Foreign gene for avian antigen |
| ▲▲▲ | Foreign marker gene |
| ▬ ▦ | Promoters |
| ░ | Non-essential region |
| — | Plasmid DNA |

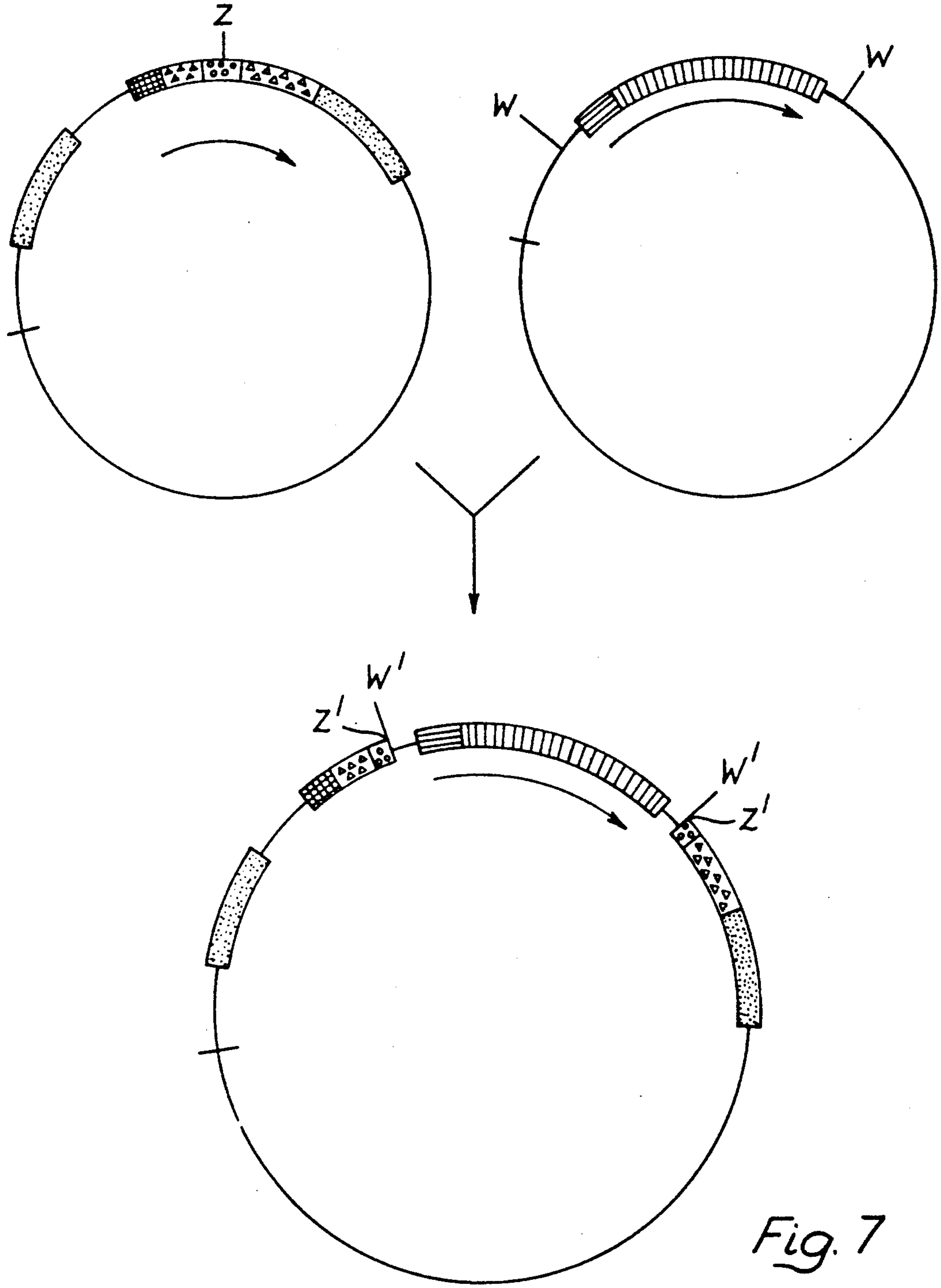
Fig. 7
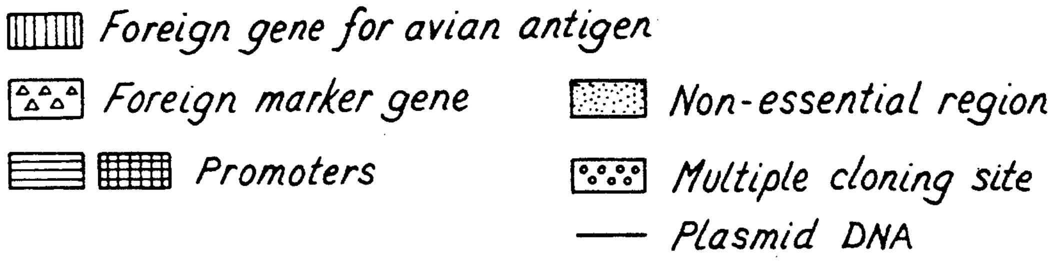

Fig. 15(a)

1 ACCCTCATCTTACGATGAGTATTTATATAGTAAAAAAAATGTATAAACAGTACCTTCCAA

61 AACCCTAATATACACATTCTTTTACCCCTTAATTTGTTAAGGTGTAAAATACCCCCTATT

121 AAAATATATATTATTGTTTTAATAAAAAAAACCATACGGTTTTACATAAAATAATACTAT

181 ATCTAATTTCCTTCCGGAAAATATTTTATAAAGCTACCCAACGTTAGCGAAAAACTTTTT

241 TATCGAGAGCTCGAGTTATACAAAAAGTTTTTATCGAGATTTCGAAAAGCTTTTTTATCG

301 AGAGCTCGAGTTATACAAAAACTTTTTTATCGAGAGCTAGAGTTATAGAAAAAGTTTTTA

361 TCGAGATTTCGAAAAGCTTTTTTATCGAGCGCTCGAGTTATAGAAAAACTTTT.......

...... continuation of combinations of blocks of repeated sequences..........

3721 .ATAGAAAAAGTTTTTATCGAGATTTCGAAAAGCTTTTTTATCGAGAGCTCGAGTTATAG

3781 AAAAACTTTTTTATCGAGAGCTCGAGTTATAGAAAAAGTTTTTATCGAGATTTCGAAAAG

3841 CTTTTTTATCGAGAGCTCGAGTTATAGAAAAACTTTTTTATCGAGAGCTCGAGTTATAGA

3901 AAAAGTTTTTATCGAGATTTCGAAAAGCTTTTTTTATCGAGAGCTCGAGTTATAGAAAAA

3961 GTTTTTTATCGAGAGCTCGAGTTATAGAAAAACTTTTTTATCGAGAGCTCGAGTTATAGA

4021 AAAACTTTTTTATCGAGAGCTCGAGTTATAGAAAAACTTTTTTATCGAGATTTCGAAAAG

↓(4101) M I V E K I
4081 CTTTTTTTTATCGAGAGCTCGAGAAGTTAAATCGAGACGCCGATATGATCGTAGAGAAAA

A A W L L Y P L C L L R C F L C N S V R
4141 TAGCGGCGTGGTTATTGTATCCGCTATGCCTTCTACGATGTTTCCTCTGTAACTCGGTAA

P A T C K C V H C L L Y P F E V C C E C
4201 GGCCCGCCACTTGCAAATGCGTCCACTGTCTCTTGTATCCCTTCGAAGTATGTTGCGAAT

M S E T L D S L E H S C C Y C C V L P L
4261 GCATGAGCGAGACGTTAGACTCTCTGGAACACAGTTGTTGTTACTGTTGCGTGCTTCCTC

L I I R E F W R R V I L P T L K A T C D
4321 TATTGATTATCAGAGAGTTCTGGAGACGCGTGATATTACCTACTCTAAAAGCGACTTGCG

C I R L P C V L T R R F C K R T I C P L
4381 ACTGTATTAGGCTACCGTGCGTTCTCACCAGAAGATTCTGTAAAAGAACCATCTGCCCGT

A K S W C R C F C C P C E V F L R C L L
4441 TAGCTAAATCTTGGTGTCGTTGTTTCTGTTGCCCTTGCGAGGTTTTCTTGAGGTGTCTCC

F P C M M L R R M H R G R L T G V R E P
4501 TCTTTCCTTGCATGATGTTGAGAAGAATGCATAGAGGCAGACTGACCGGAGTAAGAGAAC

Fig. 15(b)

```
     G  A  F  R  D  S  R  D  P  A  R  R  G  T  W  V  N  D  W  C
4561 CGGGAGCGTTTAGAGATTCAAGAGATCCCGCCAGACGGGGAACCTGGGTCAACGACTGGT

      Bgl II
     E  D  L  C  V  W  I  W  S  P  C  C  Y  V  K  R  C  I  R  T
4621 GCGAAGATCTCTGCGTATGGATATGGTCTCCGTGTTGTTACGTCAAGAGATGTATTCGCA
      ------

     M  C  D  T  F  T  K  K  I  F  Y  W  F  I  A  P  A  G  S  P
4681 CGATGTGCGACACCTTCACTAAAAAAATTTTCTACTGGTTCATCGCCCCCGCAGGATCGC

     R  M  P  E  E  P  S  P  L  S  R  K  V  F  S  S  *
4741 CGAGAATGCCCGAGGAACCTTCTCCGCTATCGAGAAAGGTCTTTTCGTCGTGAAGCATCG

4801 CGACGTGTAGATGAAAGAGATTGGACGCCAAAAGGTATACGCTCGTATTATTACGAATCG

4861 CGCTCGTCGTCGTGCCTCGAAGATGATAAAGAGAACGCGAGTAAGGAAATACAAGATAAA

4921 AACAAACTGTCGATTCTACGTAATACGATTTCTAAAACGGCGTCTACCGCAATCTTTTTC

4981 ATCAGAGTAAGGGATAGGTTAAGATTCTTAAGGACCTTTATCAAAACTATCGGAGAAAAA

5041 CTTTACGCTAAAGCCGCTCTCATGCTCTTTCACAGACTGGTGACCTATAGGCTTCCTATC

5101 GTTAGGGATATAGTCCCGTTTTATTACGCGAGGAAAAATTTTTGGAGGTTCGCTTTTCTA

5161 TATCTCATGAAGAAAGTCGCTGTTCGTCCTACTAAAAACTAATGCTAAAAAAAAATCTAT

5221 CGTTAATAAATTAAAAGTTATCGGGTTTTGAATATTATTAATCTATGCATACGAAACCGT
                                                  *  D  I  C  V  F  G  Y

5281 ACGTCGCGTTACACGGGGAGAATCCGAACGTTTTCCCGTCCGTATAGGCACACTTACCCA
      T  A  N  C  P  S  F  G  F  T  K  G  D  T  Y  A  C  K  G  V

5341 CTTCTGGTTTCTTGTCATCCCTTATCCACAAACTCTGCCCCATACCGAATTTGCTTATGA
      E  P  K  K  D  D  R  I  W  L  S  Q  G  M  G  F  K  S  I  F

                                                       Nco I
5401 ATTTCATGTCTTTTTCATTGTCTATTAGACTACGTCTAGCTAACGTACCCATGGGAAACG
                                                       ------
      K  M  D  K  E  N  D  I  L  S  R  R  A  L  T  G  M  P  F  T

5461 TTATCAAACACGTAGTCGACGCTTCGCTGTAAGTTTTTTTGTGATGCATTTTATCTAATC
      I  L  C  T  T  S  A  E  S  Y  T  K  K  H  H  M  K  D  L  R

5521 GGTTTACCCAGATACACTTATTGTTGTAAGAGGTGTACGGTCCTCTGCAATTTAGAGAGT
      N  V  W  I  C  K  N  N  Y  S  T  Y  P  G  R  C  N  L  S  N

5581 TAGCGCAATCCAACATTAACAACATCGCTATCAAGATTAATGATTTCATTTTGATACACG
      A  C  D  L  M  L  L  M  A  I  L  I  L  S  K  M

5641 GATCAATTTTAATAGTCTATAGAGATATACCCCACCAATAGTTACGCGATTAATTTTCAA
```

Fig. 15(c)

```
5701 TTATACATAATAAAAATCTAGAGGAGTTGCCATGTGATTCTCTGTCGACGACGTTACCTC

5761 GTTAGTTTTATTAATTCTTCTTTAAGTTCTGACGACGGTTATATACCAAAACAGCTTTTA

5821 CTTTTCGTAAGACGATAATTACGTTATAAAAGATTAAGAAATTTTATTTTTACTAAAGTA

            M  N  N  D  T  I  F  T  L  F  Y  C  K  N  K  K  Y  V  R  G
5881 TCATGAATAATGACACGATATTTACTTTGTTTTATTGTAAAAATAAAAAATATGTTCGTG

     E  G  G  R  R  R  G  K  T  G  I  L  L  F  H  P  I  N  H  R
5941 GGGAGGGGGGAAGGAGGAGAGGGAAGACGGGTATCCTTTTATTCCATCCAATAAACCACC

              Spe I
     V  I  G  T  S  A  H  Q  C  Y  K  T  R  R  I  G  F  K  L  Y
6001 GTGTTATAGGAACTAGTGCACATCAGTGTTATAAAACACGAAGAATCGGTTTCAAACTCT
                  -----

     A  V  A  P  R  H  V  S  T  I  R  C  G  R  S  H  S  A  H  R
6061 ACGCAGTTGCCCCTCGTCACGTATCCACTATCCGCTGTGGGAGATCCCACTCGGCTCACC

     V  D  K  F  S  F  S  F  Q  K  V  D  F  H  C  I  A  G  S  G
6121 GAGTAGATAAGTTCTCCTTCTCCTTCCAAAAAGTAGATTTTCACTGTATCGCCGGCAGCG

     A  *
6181 GCGCATAGGTATCTGGCCCTACAGAATTCCATATTCCTGATAGCTCGCGCGACGAAGCCT

6241 CCGTCGCCCGTGTGATCATTTTCATAATTCAAGGGGATCC (6280)
```

FOWLPOX VIRUS NON-ESSENTIAL REGIONS

BACKGROUND OF THE INVENTION

1. Field of the Invention

This invention is in the field of recombinant DNA technology and relates to fowlpox virus as a vector for foreign DNA.

2. Description of the Prior Art

Several viruses with DNA genomes have been used to carry and express genes from other viruses or other species. Viruses used in such a way are known as 'vectors' and genes, other than their own, expressed in such a way are referred to as 'foreign genes'. One of the primary requirements for a virus to be used as a vector in this manner is a suitable site for insertion of the foreign gene. If insertion of a gene into a site in the virus causes disruption of some function essential for growth, then such a site could not be used. Suitable sites are those at which an insertion does not disrupt any functions or those whose functions are not essential for viral growth and therefore can be disrupted with impunity. Such sites are known as 'non-essential regions'. The phrase 'non-essential' in this context means non-essential for growth under at least some conditions in which the virus can be grown in vitro and under at least some conditions in which it survives in vivo.

Examples of viruses which have been used as vectors by virtue of the fact that they contain non-essential regions are orthopoxviruses, adenoviruses and herpesviruses, although the regions used may be different in each case. Vaccinia virus (VV), which has been used as a vector, is an orthopoxvirus, a member of the pox virus family. Fowlpoxvirus (FPV), the subject of this patent application, is also a pox virus, but is a member of a different genus, the avipoxviruses. VV can be grown in tissue culture, and foreign genes can be inserted into the viral genome during this process. Several regions of VV have been found to be non-essential in vitro in more than one tissue-culture system. These include: large regions towards the left hand end, B. Moss et al., J. Virology 40, 387-395, (1981) who describe a mutant VV having a deletion 6.4 megaDaltons from the left-hand end; D. Panicali et al., J. Virology 37 1000-1010, 1981) who describe a mutant VV having a deletion starting 6.85 megaDaltons from the left-hand end; the thymidine kinase (TK) gene, D. Panicali and E. Paoletti, Proc. Natl. Acad. Sci. USA 79, 4927-4931 (1982); M. Mackett et al., J. Gen. Virol. 45, 683-701, (1982); and the vaccinia growth factor (VGF) gene, R. M. L. Buller it al., J. Virology 62, 866-974 (1988). Sites such as these might also be non-essential for growth in vivo. However in the case of both the TK and VGF gene, it has been found that although growth in tissue culture is unaffected or only slightly affected by insertion into the gene, growth and virulence in vivo are markedly affected, R. M. L. Buller el al., Nature 317, 813-815 (1985) and loc. cit. (1988), showing that these genes are not completely non-essential for growth of the virus in vivo. This in vivo attenuation may however be useful if it reduces unwanted pathogenic effects of the virus and accordingly growth in vivo with accompanying attenuation is a valid growth condition for the purpose of this invention.

Some sites are essential in some tissue culture systems and non-essential in others. For example there is a gene in VV which is essential for replication in human cells but which is non-essential in chicken embryo fibroblast cells, S. Gillard et al., Proc. Natl. Acad. Sci. USA 83, 5573-5577 (1986). Another gene in the related orthopoxvirus cowpox virus is essential for growth in chinese hamster ovary cells but not for growth in chicken embryo fibroblast cells, D. Spehner et al., J. Virology 62, 1297-1304 (1988). These examples show that differences in the tissue culture systems can affect which regions are non-essential.

The VV genome is far from being completely mapped and relatively little has been published about the FPV genome. It is known that FPV has a TK gene which has about 60% homology with the VV TK gene at the amino acid level , D. B. Boyle et al., Virology 156, 355-365 (1987). Like the VV TK gene, it serves as a non-essential region for homologous recombination under at least some conditions: see PCT Application WO 88/02022 (CSIRO). Using the *E. coli* xanthine-guanine phosphoribosyl transferase (Ecogpt) gene as a dominant selectable marker, in conjunction with the VV "7.5" promoter, the influenza haemagglutinin (HA) gene was inserted into a TK region of FPV and the FPV grown in chicken embryo skin cells. Expression of the HA gene was demonstrated by the binding of HA antibodies and labelled protein A to plaques of recombinant FPV.

The genome of FPV is known to have other similarities to VV in some regions. For example the DNA polymerase genes are closely related, having 42% homology at the amino acid level, M. M. Binns et al., Nucleic Acids Research 15, 6563-6573 (1987). On the other hand, F. M. Tomley, in a talk at the 6th Workshop on Poxvirus/Iridovirus, Cold Spring Harbor, N.Y., Sep. 24-28, 1986, described an attempted correlation of an 11.2 kb fragment of FPV DNA, located near one end of the genome, with VV DNA. While she reported 25% amino acid homology between a gene predicting a 48 kd polypeptide in FPV and a gene in VV coding for a 42 kd polypeptide, no other match of any significance was found. More detail of this work is given in F. M. Tomley et al., J. Gen. Virol. 69, 1025-1040 (1988).

F. M. Tomley et al, quoting M. Mackett and L. C. Archard, J. General Virology 45, 683-701 (1979), also state at page 1038 that the terminal portions of orthopoxvirus genomes are less well conserved than the central region and also say that the terminal regions, of around 30 to 35 kb in length, are thought to encode genes which determine specific virus characteristics such as host range, virulence, tissue tropism and cytopathogenicity and are thus less likely to be conserved.

The terminal region of VV is known to be of possible interest in relation to non-essential regions. Thus, M. E. Perkus et al., Virology 152, 285-297 (1986), have found that deletions in the VV genome occur in the presence of bromoxydeuridine, one of which extended from about nucleotides 2700 to 24100 from the left-hand end and that the deletion mutant virus is viable in tissue culture (cell type not clearly stated). Some information has been released about the very terminal region of FPV, in a poster by J. I. A. Campbell displayed at the International Poxvirus Workshop, Cold Spring Harbor, N.Y., Sep. 9-13, 1987. (The poster gives more information than does the abstract published in "Modern Approaches to New Vaccines including Prevention of AIDS", CSH 1987, page 45). Like VV and cowpox virus, FPV has terminal sequences which are inverted repeats of each other and are covalently cross-linked together. A part of the terminal inverted repeat (TIR)

sequence was digested with BamHI and cloned. The BamHI fragment was described as having a length of 6.3 kb. The poster describes the general layout of the sequences, which from left to right comprise a short unique region, a set of tandemly repeated sequences and then a long unique region containing three possible open reading frames. The summary notes that this FPV terminal fragment shares the general pattern of nucleotide sequence with the terminal fragments of VV and cowpoxvirus, but also notes some marked differences. The sequence of part of the VV TIR, namely from approximately nucleotides 6800 to 9000 from the left-hand end, VV i s reported by S. Venkatesan et al., J. Virology 44, 637-646 (1982).

Large differences between the DNA sequence of VV and FPV are to be expected, since the FPV genome is estimated to be at least one third longer than that of VV. It seems likely, from the present knowledge as cited above, that many of the differences between the genomes of FPV and VV will be nearer to the termini than to the center of the genome. Thus, information about the terminal region of VV is of limited interest in relation to FPV.

It has been a problem to locate a well-defined non-essential region other than the TK gene, in fowlpox virus. Very recently (Apr. 20, 1989), in PCT application publication No. WO89/03429 (Health Research Inc.), FPV recombinants have been described, but the non-essential regions mentioned therein are not all well defined. The recombinants were generated merely by cleaving the FPV gene into fragments and trying the fragments with test constructs to see whether the foreign gene under test was expressed.

The VV HindIII-D fragment is one of the best characterised regions of the virus. The sequence of this 16060bp fragment has been determined, Niles et al., Virology 153, 96-112 (1986), and thirteen genes (D1-D13) have been identified.

Several temperature-sensitive mutants have been mapped to genes within HindIII-D and fine mapping has assigned these to D2, D3, D5, D6, D7, D11 and D13, Seto it al., Virology 160 110-119 (1987). These genes are therefore essential for virus replication. It is not known whether the remaining genes within the VV HindIII-D fragment are essential or non-essential for virus growth. Recent experiments have suggested (though not proved) that D8, which encodes a trans-membrane protein, might be non-essential for propagation of vaccinia virus in tissue culture, Niles and Seto, Journal of Virology 62 3772-3778 (1988). In these experiments, a frameshift mutation was introduced into the carboxy-end of D8 which removed the carboxy-terminal 56 amino acids of D8. Virus containing this mutation had growth rates indistinguishable from those of wild type virus.

It was not predictable, however, whether the D8 gene would occur in fowlpox virus and if so whether it would be non-essential. Moreover, there was the problem of how to locate the D8 gene in the FPV genome which is relatively unmapped and is much larger than that of VV. Consequently, examination of the vaccinia Virus HindIII-D fragment did not indicate how to find further non-essential regions within FPV.

SUMMARY OF THE INVENTION

It has now been found that the three open-reading frames (ORFs) wholly within the above-mentioned BamHI fragment of the terminal inverted repeat (TIR) are non-essential regions which can serve as sites for homologous recombination events whereby a foreign gene can be introduced into FPV (refer to FIG. 1). These ORFs are characterised in that they have lengths of approximately 670, 370 and 300 nucleotides and fall within the long unique sequence (LUS) of the TIR within the BamHI fragment. The BamHI fragment has been found to have a length of about 6.3 kb and the long unique sequence begins at approximately nucleotide 4100, numbering from the left-hand end. (As to nucleotide numbering, please refer to the cautionary note in the discussion of FIGS. 15(*a*)-15(*c*) below. The lengths of the ORFs can also be expressed in terms of the approximate molecular weights of the polypeptides which they are predicted to encode, namely 26.0, 13.9 and 11.5 kilodaltons. This nomenclature will be used hereinafter for identification purposes. The 26.0 and 11.5 genes are coded for on the same strand and in that order when reading the fragment left to right from the 5' end towards the BamHI site, the 11.5 gene having its 3' near the BamHI site (see FIG. 3). The 13.9 gene is encoded on the complementary strand, reading right to left, but within a region distinct from and lying in between that coding for the 26.0. and 11.5 genes on the first strand.

Extrapolation from this and other findings leads to the reasonable suppositions that the whole of the long unique sequence of the TIR is a non-essential region, including sequence lying to the immediate right-hand end of the BamHI site, i.e. within the 11.2 kb fragment sequenced by F. M. Tomley et al., loc. cit. (1988). The TIR has a length of about 10 kb, i.e. 10−6.3 =3.7 kb lies within the 11.2 kb fragment. Thus, the long unique sequence extends to the right from about nucleotide 4100 over the remaining lengths of TIR, of about 6 kb.

Accordingly, in an important aspect the present invention provides a recombination vector for use in producing a recombination fowlpox virus (FPV) by homologous DNA recombination, said recombination vector comprising a cloning vector containing a non-essential region (NER) sequence comprising at least part of the long unique sequence (LUS) of the terminal inverted repeat (TIR) of FPV, said NER being interrupted by a foreign gene or genes and by a sequence or sequences for regulating the expression of each foreign gene present. Preferably the NER is within part of the long unique sequence (LUS) lying within the 6.3 kb BamHI fragment. In a more particular aspect, the NER consists of at least a homologously recombinable length of an open reading frame (ORF) having a length of approximately 670, 370 or 300 nucleotides and falling wholly within that part of the LUS within the BamHI fragment of the TIR. However, we have also found that some isolates of the same strain of FPV do not have a lengthy sequence of over 200 bp of DNA spanning the BamHI site, which is an important pointer to the non-essentiality of the sequence spanning that site. It is therefore inappropriate to use the terminology "BamHI fragment" in a formal definition applicable to FPV generally. Accordingly, these ORFs are better defined as lying within the first 2.2 kb of the LUS after the tandem repeats, that is to say within 2.2 kb of its external end. NERs within this 2.2 kb are preferred. The above preferences for location of NERs apply also to the flanking sequences contained in the recombination vector and this invention, i.e. all the homologously recombinable sequence which flanks the foreign gene(s) and their regulatory sequence(s).

We have also found certain other non-essential regions of fowlpox virus. Whereas those described above are within part of the terminal inverted repeat, these further regions are in a more central part of the FPV DNA molecule, namely within or adjacent to one end of a 6.3 kb fragment of an EcoRIl ibrary of FPV, the genes of which show significant degrees of homology with certain genes of the vaccinia virus (VV) HindIII-D fragment.

This second aspect of the present invention has its origins in a random cloning of parts of the FPV genome, sequencing of the random clones and a search in all six reading frames for possible open reading frames which might predict genes. The sequences thus generated were compared with vaccinia virus (VV) protein sequences. It so happened that degrees of homology were noted to some of the VV proteins D1–D13, including approximate matches to VV D1, D5, D9, D10 and D13. It was therefore decided provisionally to adopt the "D" terminology for the FPV genes which showed some degree of homology with the VV genes. An M13 clone of FPV matching VV D9 was used as a probe to identify clones within an EcoRI library of FPV. One such clone, designated pMB379, containing a 6.3 kb insert, was sequenced. This clone contained part of the D9 gene and all of D10, D11, D12 and D13. (The last four genes showed 40%, 62%, 53% and 55% identity of amino acids encoded to their VV homologues). In order to clone D7 and D8 genes, a DraI library of FPV DNA cloned in the plasmid pUC13 Sm 1 was constructed. Colonies were probed with a prime-cut probe derived from an M13 clone designated M379-27S (which lies within the FPV D9 gene) and one positive colony, containing a plasmid designated pMB389, was studied further. pMB389 was found to contain the "carboxy"-end of the D6 gene, entire D7, D9, D10 genes and the "carboxy"-end of the D11 gene. (D11 runs in the reverse direction to D10, so the carboxy end is that nearer to D10. The "carboxy" end is that which is the 3'- end of the coding strand, corresponding to the carboxy end of the predicted polypeptide). There was no identifiable homologue of the VV D8 gene, although another gene was present between D7 and D9. This has been termed "D8" as a matter of convenience. In a particularly unexpected finding, the copy of D9 present in both pMB379 and pMB389 possessed frameshift mutations when compared with its VV counterpart, thus making it unlikely that D9 is expressed in FPV.

It has now been found that the D8 and D9 genes of FPV are non-essential genes which can be used for the insertion of foreign DNA. Since the intergenic regions can also be considered non-essential, it follows that in principle the whole of the region following the carboxy-end of D7 and up to the carboxy end of the D9 gene is a non-essential region (NER). (The genes D7, D8, D9 and D10 all run in the same direction). However, as will be explained hereinafter, the NER does not run right up to the carboxy-end of the D9 gene, but stops short thereof in order to avoid possible interference with the D10 gene, which overlaps with the D9, and the promoter of the D10 gene. This NER will be referred to hereinafter for brevity as the D8–D9 NER.

Accordingly, the present invention further provides a recombination vector as set forth above but wherein the NER is such a carboxy end-D7 to near carboxy end-D9 region NER (but excepting the D10 gene and D10 promoter region).

In a second important aspect the invention provides a recombinant vector, e.g. a plasmid, containing a NER sequence (TIR or D8–D9) as defined above. Such a vector is useful for preparing the above-defined recombination vector.

Thirdly, the invention includes a DNA molecule which consists substantially or essentially of a NER sequence as defined above with or without some homologously recombinable flanking sequence, say (arbitrarily) up to 1000 bp per end at either or both ends thereof in order to distinguish such a molecule from the genomic DNA of FPV.

Fourthly, the invention covers a host, appropriate to the vector, harbouring any of the vectors of the invention, i.e. the recombination vector or any intermediate vector which contains the novel NER sequence.

Fifthly, the invention embraces a recombinant FPV produced by homolgous recombination of a parent FPV with the insert DNA of a recombination vector defined above.

Sixthly, the invention includes animal, especially chicken, cells infected with the above-identified recombinant FPV, a process of in vitro culture of said cells and, where patent law permits, a method of vaccinating a responsive animal, especially a chicken, with the recombinant FPV.

In a more particular aspect the recombination vector of the invention comprises in order:

(1) a first homologously recombinable flanking sequence, (2) a sequence within a first portion of the non-essential region, (3) promoter DNA, (4) a foreign gene transcribably downstream of the promoter (whereby when the fowlpox virus RNA polymerase binds to the promoter it will transcribe the foreign gene into mRNA), (5) a sequence within a second portion of the same non-essential region, the first and second sequences being in the same relative orientation as are the first and second portions of the non-essential region within the viral genome, and (6) a second homologously recombinable flanking sequence.

BRIEF DESCRIPTION OF THE DRAWINGS

FIG. 4 to 7 illustrate schematically various general methods of construction of recombination plasmids in accordance with the invention.

FIGS. 15(*a*) to 15(*c*) show the DNA sequence of the BamHI fragment starting from the left hand end, reading in the 5' to 3' direction.

DESCRIPTION OF THE PREFERRED EMBODIMENTS

Figure 2:
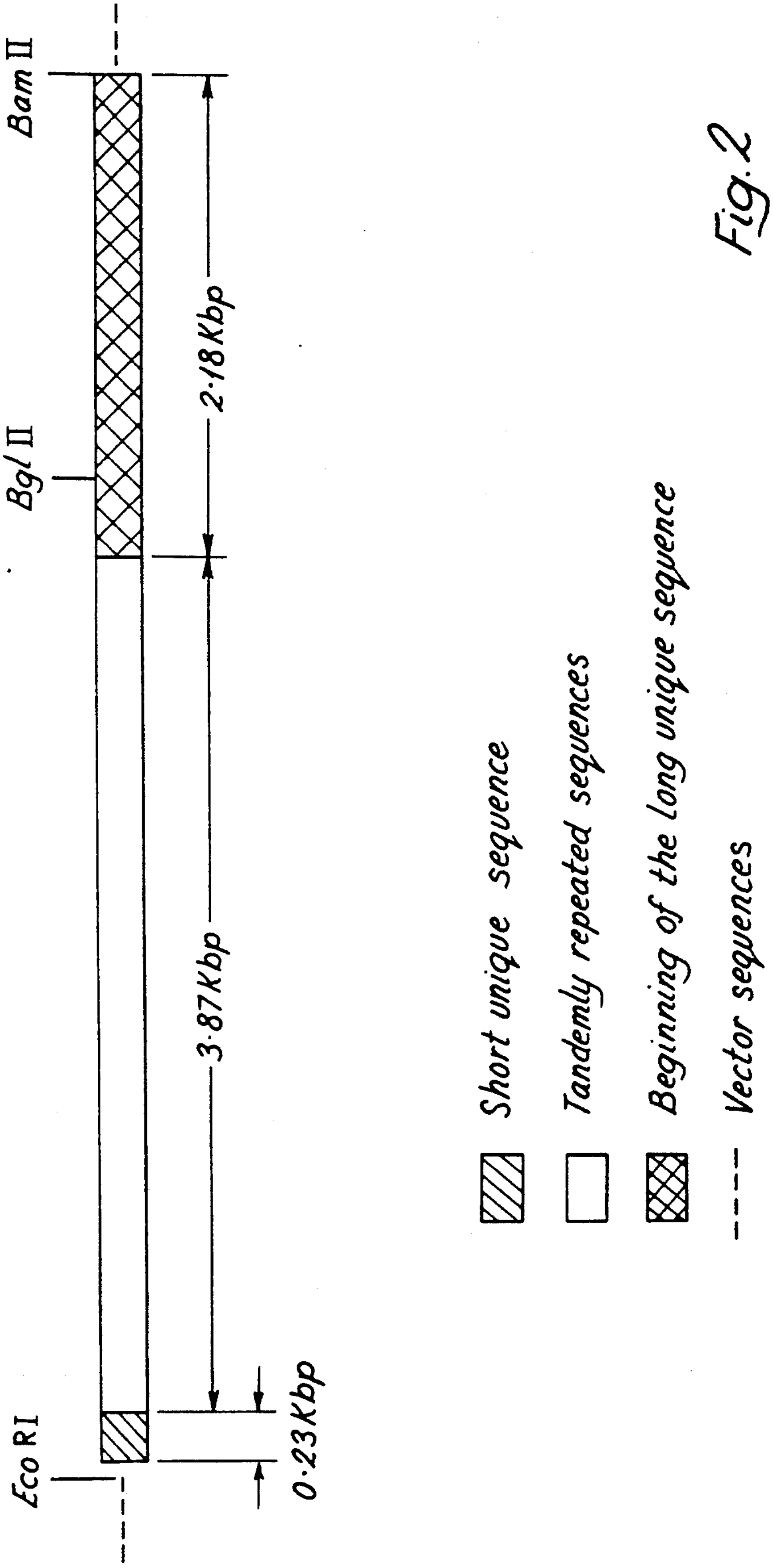
FIG. 2 is a map of the BamHI terminal fragment of FPV DNA showing the location therein of the beginning of the long unique sequence of the TIR.

Referring first to the terminal inverted repeat (TIR) NERs and to FIG. 2, the BamHI fragment of the TIR of FPV has a length of about 6.3 kb. It contains a short unique sequence of length 0.23 kb, followed by a region of approximate length 3.87 kb which contains tandemly repeated sequences and then a long unique sequence of length 2.18 kb.

Figure 3:
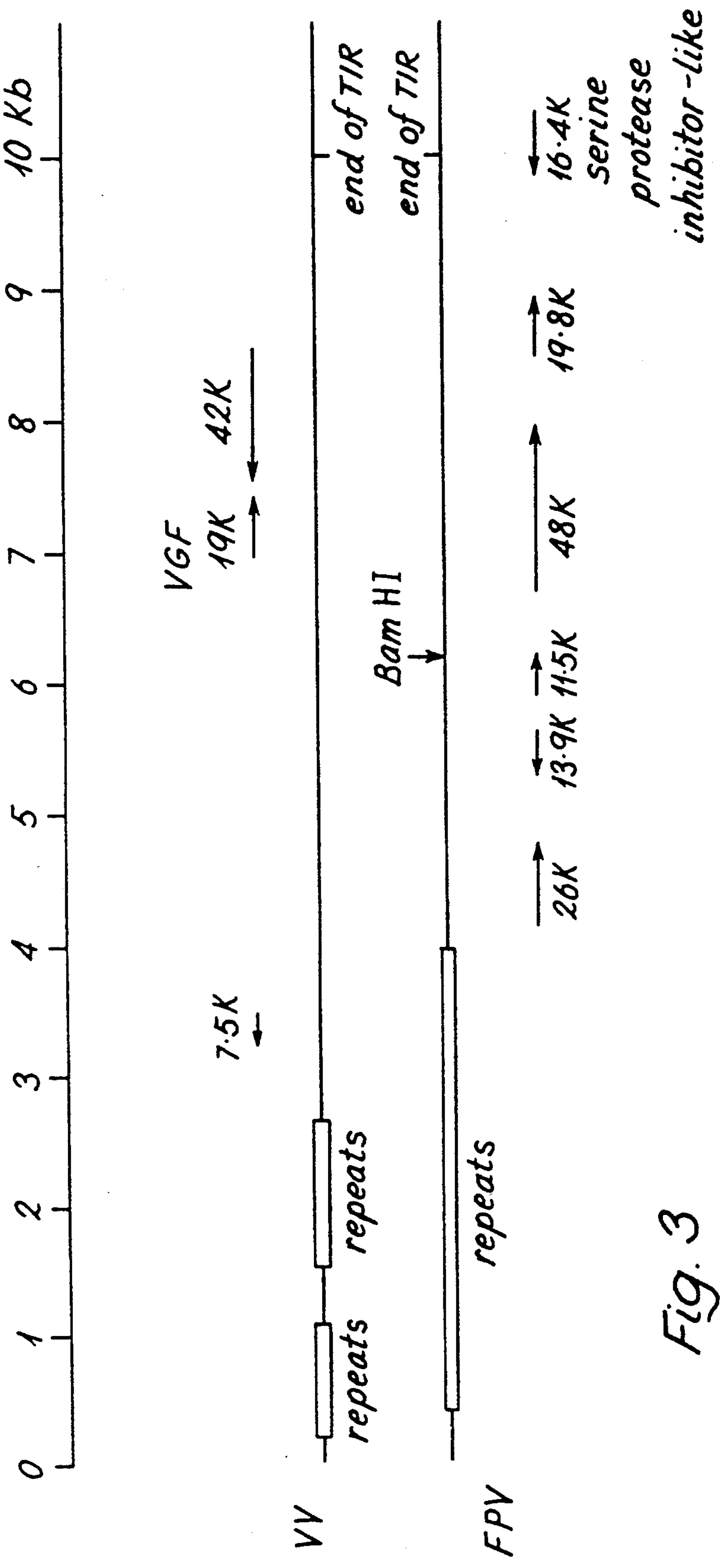
FIG. 3 is a DNA map of the FPV TIR showing three non-essential region sequences useful in the present invention and other ORFs, together with a map of the VV TIR showing the different ORFs found in VV.

The approximate location of the genes providing the TIR NER DNA for use in the invention within the BamHI fragment is shown in the map of FIG. 3. The arrows show that the 13.9 gene is on a complementary strand. From this map and from sequence information it will be seen that these genes have no known near counterpart in VV. The BamHI site is believed to be part of a further non-essential region for the reasons explained above. A total of five ORFs have been found in the long unique sequence of the TIR. Those which appear to encode polypeptides by virtue of their distinctive FPV codon bias occur as follows:

| Location (Nucleotides numbered from left-hand end) | No. nucleotides | No. amino acids encoded | M.w. of polypeptide | Unique site |
|---|---|---|---|---|
| 4125-4790 | 666 | 222 | 26.0 kd | Bgl II |
| 5261-5629C | 369 | 123 | 13.9 kd | Nco I |
| 5883-6185 | 303 | 101 | 11.5 kd | Spe I |

C=occurs on the strand complementary to that shown in the nucleotide sequence below.

Besides the three ORFs designated 26.0, 13.9 and 11.5, there are two shorter ORFs on the complementary strand. Since, however, neither of these ORFs exhibit the required FPV codon bias it is unlikely that they code for genes.

FIGS 15(*a*)-15(*c*) show the DNA sequence of the BamHI fragment, starting from the left-hand end and reading in the usual 5' to 3' direction, together with predicted polypeptides encoded. It should be borne in mind, however, that the sequencing of the tandemly repeated region has presented difficulties and that the number of nucleotides within this region might be subject to some revision. This is not a matter of any significance to the present invention, which is not concerned with the tandemly repeated region. It follows that the long unique sequence does not necessarily start at about nucleotide 4110 in absolute numbering and the nucleotide numbers are therefore to be treated as merely guidance to the reader to enable him to identify the ORFs referred to and to be construed accordingly in the description and claims. It will be appreciated that the sequence shown in FIGS. 15(*a*) to 15(*c*) definitive of FPV generically, since there will inevitably be small variations between different types or strains of FPV, some of which might take the form of deletions or insertions, and any variant NER compatible with the desired homologous recombination is usable herein. In particular, DNA having a NER sequence based on ORFs having a sequence showing at least, say, 90% homology with the sequence set forth above is a preferred feature of the invention.

Beyond the BamHI site (GGATCC) the nucleotide sequence continues as per F. M. Tomley et al. loc. cit. (1988) at page 1029, nucleotide 6275 shown above being the first of the BamHI recognition sequence and No. 1 in Tomley et al.'s numbering. While there are no ORFs spanning the BamHI site, the sequence extending at least as far as the first 160 bp into the ( 11.2 kb fragment of Tomley et al. is demonstrable non-essential, while further sequence thereafter is likely to be.

The NERs of the invention can be used to insert foreign genes into FPV. It is desirable that the gene be stably incorporated so that the resultant recombinant FPV can be repeatedly cultured in tissue culture on a large scale. Evidence to date is that the 13.9 gene is less stable than the other two.

The foreign gene can be inserted at any location within the NER sequence of the recombination plasmid. Preferably it is not so excessively near one end or the other as not to provide a site long enough for homologous recombination with the corresponding NER of the wild type FPV. However, it is possible to allow homologous recombination to occur outside the NER by providing, in the recombination vector, flanking sequence lying beyond either or both ends of the NER. It is probably not usually beneficial to use flanking sequences which are heavily tandemly repeated, since this will increase the chances of unwanted recombination events. Thus, it is suggested that flanking sequences running extensively beyond the external end of the LUS into the tandem repeat region are best avoided.

Figure 9:
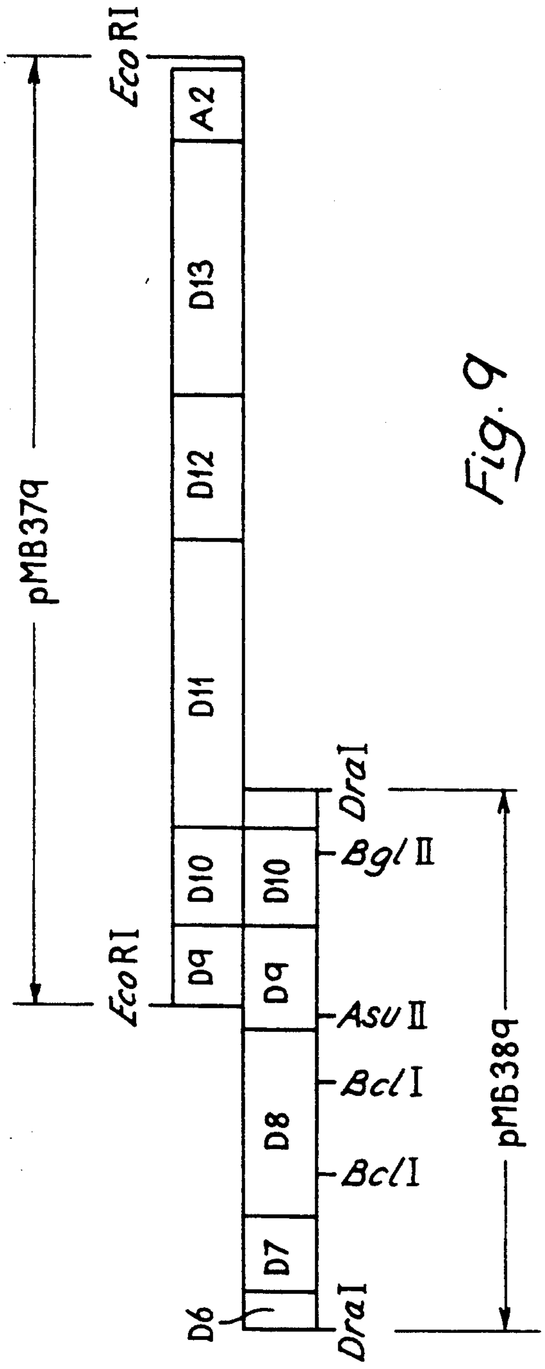
FIG. 9 is a map of the genes D6 to D13 and an adjacent gene A2 showing the genes cloned in plasmids pMB379 and 389 and important restriction sites in these plasmids.

Referring now to the D8-D9 NER and to FIG. 9 of the drawings, the plasmids pMB379 and pMB389 have FPV DNA inserts which overlap in the D9 and D10 gene region. By sequencing these inserts a long nucleotide sequence has been obtained which runs from the 3'-end of D6 through to D13 and beyond that to the adjacent A2 gene.

In the sequence shown below, those parts which are not relevant to the present invention have been truncated. The restriction sites DraI (TTTAAA), EcoRI (GAATTC), BclI (TGATCA), AsuII (TTCGAA) and BulII (AGATCT) used in the cloning and construction of plasmids for testing out non-essential regions are underlined. The amino acid sequences of predicted genes are given in the single letter code. The D9 gene, being considered to be unexpressed in FPV, is not given an amino acid sequence, but is considered to run from nucleotides 1298 to 1984. Start and stop codons have been underlined. The sequence shown encompasses the carboxy end of the D7 gene and the carboxy end of the D11 gene. (Since the D11 gene has an open-reading frame running in the reverse direction to the others, its near-D10 end is that encoding the carboxy terminus of the putative D11 protein). The sequence shows the DraI site in the D11 gene (see also FIG. 9).

It will be seen that the D10 gene starts within the end of the D9 gene, being within a different reading frame. The D10 promoter is therefore also within the D9 gene. The non-essential region is therefore defined as extending up to the beginning of the D10 promoter region, which is estimated at approximately 35 bases before the ATG start codon for D10, i.e. at around nucleotide 1936.

D7 (carboxy-terminus)

```
        A   Q   S   G   M   E   S   S   F   V   F   L   G   N   I   I   E   K   *
   1 AGCCCAATCTGGAATGGAATCATCTTTTGTTTTCTTAGGTAACATAATTGAAAAATAATA

  61 CTTTAATAAAGATTAATTTACATAATACCTACATCATGTAACGTATAGCTTATTAAACAT

 121 GGATAGCATTTAGTAATATTTGTAAAATCAAAAATAACTATAAATATTTTAATAGTATAT

 181 TGAATTCTTTATCATGTAGAAAGATATTAGTTATACACACAATGATATGTAAAAATAGTA

 241 TTCGACATAAAGAATTGACGTTGATAATATTTCTCTGCTTTATATATCTATCAAAAACTT

 301 TTGTAGAAGTAAAAGCACCTCCCTATGTACTCGTACCGGAAGTAGTGATATAAATCTTAC

 361 TTGTTTTATTAAAGATGATCAGGGTGCTGGAGAAGATAAAGTAATTGTAGCGTGGCAACA

D8               M   L   H   I   S   K   V   S   K   E   A   E   G   S   Y   M   C   V
 481 CCAAACCATGCTACATATATCCAAGGTATCTAAAGAAGCAGAAGGTTCATATATGTGTGT

       V   W   I   N   G   D   A   D   Y   K   K   M   N   L   G   V   F   T   V   S
 541 TGTATGGATAAACGGCGACGCTGATTATAAAAAAATGAATCTAGGAGTGTTTACTGTTTC

       K   K   T   Y   M   H   N   E   V   S   I   T   P   R   R   S   R   V   D   M
 601 AAAAAAAACCTACATGCATAACGAAGTAAGTATAACCCCTCGAAGATCGAGAGTAGATAT

       S   D   G   R   P   L   K   I   E   C   A   F   S   T   R   R   I   Y   G   R
 661 GTCGGATGGTCGGCCGCTAAAAATTGAATGTGCTTTTAGTACCCGACGAATATATGGTAG

       S   Q   V   N   I   K   W   W   K   I   D   G   I   T   R   K   W   E   Q   Q
 721 AAGCCAAGTCAACATAAAATGGTGGAAGATTGACGGTATTACACGAAAATGGGAACAACA

       T   S   G   V   N   L   L   L   H   T   Y   G   G   I   G   S   L   S   I   P
 781 GACTTCGGGAGTTAACTTACTGTTACATACTTATGGAGGGATAGGATCGCTAAGTATCCC

       N   P   T   T   G   E   S   T   G   K   Y   M   C   V   V   T   C   G   D   I
 841 AAATCCTACAACAGGAGAATCAACAGGTAAGTATATGTGCGTAGTTACCTGTGGAGATAT

       G   N   V   G   F   R   L   V   K   S   L   S   P   L   S   D   T   E   S   D
 901 TGGAAATGTTGGATTTAGACTGGTAAAATCATTATCTCCTTTATCAGATACAGAATCTGA

       H   S   Y   T   S   E   E   G   S   H   F   M   E   R   C   K   V   K   K   S
 961 TCATAGTTATACTTCAGAGGAAGGATCACATTTTATGGAAAGATGCAAAGTCAAAAAAAG

       P   Y   G   G   W   I   V   E   *
1021 TCCGTACGGTGGATGGATAGTAGAATAGATCATCTCAGGGACGCGGTATATATTGCTATA

1081 AAGTAAAATAATTTCTCAATACATTTTTCTACTTTAACGATATAATCGTTAACTTATTAG

1141 TTTAATTATATCATATATTCCTTTATATCTTAATTAAAAAAATATATTCATAAATGGGAT

1201 ACACTAGTATTTTTTTATATAGTTTACGATATGCTATTTCACTATATATAGTTTATCAAA

1261 CATAAGTGAAAAATAAACAACTATAAAAACTAAGATCATGTTCGATATATCCAGAGAACA

1321 ACAAAATATATTAGAAAAAAATAAAGATTGTGTTATTACTTTCGAAACAAATAAAGAATA

1381 ACTATAGAAAACACTAACATAAAAGATATACTTAGCGATAGACGAATTCACATATCGCGT

1441 TATGTATTACATCAGATAATATACCTATAATCGGTATAAGAAGAACGTCTTTTATGTATC

1501 AATCGGTTATATCAAAAAGAAGAAGCTTTTCAGAAATATTAGCCGTCGAT TAAACCATC

1561 TAAAGTATATGTATAATAACGAAATTAAAGAAATATCATTAGATCAATAGTACCATTCAC

1621 ATATAGCGGATTCAACAACTTTGAAGAGTTAGTATTATTAGGAGGAAGAGTTAAAAATAA

1681 AGAATCAATATATCAATGCCTGAGTAGAGAACTATCGGAAGAAAGCGATGGAATACTTAC

1741 TATAAAAACATTTGGTAATAAAATATTAAAACTTACCATAGAAGATAAGATACTTCGTAG

1801 AACATTTTATGGGTATTGTATAGTGTGTTTTATAGACCAACTCTATTCAGAAATCATTAA

1861 ACCTTTATATAACATAGAAATCAAAGAATTAGGATCATTATTTGATCGATCAAGTAATGA

D10                                                      M   G   E
1921 AAAATACGAATACTTGCATTTTATTTATAATACCTTATTAACATATAAATATGGGGGAGT
```

-continued

```
     Y   Y   K   N   K   L   L   L   R   P   S   V   Y   S   D   N   I   Q   K   I
1981 ATTATAAAAATAAATTGCTCCTTAGGCCGTCTGTATATTCTGATAATATACAAAAAATCA

     K   L   V   A   Y   E   Y   G   K   L   H   A   K   Y   P   L   S   V   I   G
2041 AACTGGTAGCATATGAATATGGCAAACTACATGCTAAATATCCACTATCCGTAATAGGTA

     I   M   K   T   I   D   D   K   F   V   L   C   H   R   Y   N   S   F   L   F
2101 TAATGAAAACAATAGATGACAAGTTTGTTTTATGCCATAGATACAATAGTTTCTTGTTTT

     S   E   I   A   F   T   K   D   K   R   R   K   I   R   L   F   K   K   Y   S
2161 CAGAAATAGCATTTACAAAAGATAAACGACGGAAAATAAGACTCTTTAAGAAATATTCAA

     K   Y   M   S   N   I   E   R   D   I   L   S   Y   K   L   S   L   P   N   N
2221 AGTATATGAGTAACATCGAACGTGATATATTAAGTTATAAGCTATCGCTTCCTAATAACT

     Y   N   T   N   H   I   D   I   I   F   P   G   G   K   I   K   D   L   E   S
2281 ATAATACAAACCATATAGATATAATCTTCCCAGGTGGTAAAATAAAAGACTTGGAAAGTA

     I   T   N   C   L   V   R   E   I   K   E   E   L   N   I   D   S   S   Y   L
2341 TAACTAATTGTCTAGTAAGAGAAATAAAAGAAGAATTAAATATCGATTCCTCTTATCTCG

     A   I   C   K   N   C   F   V   Y   G   S   I   Y   D   R   L   I   D   K   D
2401 CTATCTGTAAGAACTGTTTTGTATACGGTTCTATATACGACAGATTGATAGATAAAGATT

     F   E   V   I   A   L   Y   V   E   T   D   L   T   S   R   Q   I   L   N   R
2461 TTGAAGTTATAGCCCTTTACGTAGAAACAGATCTTACGAGTAGACAAATATTGAATAGAT

     F   I   P   N   R   E   I   K   G   I   S   F   I   D   A   R   D   I   N   K
2521 TCATCCCTAATAGAGAAATTAAAGGAATATCATTTATAGACGCAAGAGATATTAACAAAG

     D   Y   L   Y   T   N   V   I   K   Y   I   I   N   A   V   R   T   S   A   S
2581 ATTATTTGTATACTAATGTAATTAAATATATAATAAACGCTGTAAGAACATCCGCTAGCA

     N   S   *
2641 ATAGTTAACATCTATCTAACTGTTAATATATAAATTAATTT . . . .
D11                  *   R   V   T   L   I   Y   I   L   K
(carboxy-terminus)

2881 . . . . . . TAATTTTTTAAACCC. . .
                  L   K   K   F   G
```

There are some preliminary indications that the insertion of a foreign gene in the D10 gene is unstable. Accordingly the D10 gene is not a NER for the purposes of the invention.

Referring now to all the NERs of this invention, the recombination vector can contain a reasonable length of homologously recombinable flanking sequence to each side of the NER, preferably at least 100 nucleotides, more preferably at least 250 nucleotides and still more preferably at least 500 nucleotides. On the other hand, in the interests of not making the insert for the recombination vector too large, it is often desirable to limit such flanking sequence outside the NER to, say, not more than 1000 bp.

Incidentally, precise homology of the flanking sequence and the NER is not necessarily required. Remarks to that effect in WO 89/03429 apply here also.

In preparing recombinant FPV of the invention, the first requirement is for a promoter. The well-known vaccinia virus P7.5 promoter the H6 promoter (see the cited PCT application publication No. WO 89/03429) or the P11 promoter, can be used, as these are accepted by the FPV as compatible. Preferably, however, a FPV promoter is used. Certain promoters have been described in the prior PCT patent application publication No. WO 89/03879 (National Research Development Corporation), the contents of which are herein incorporated by reference. The "4b" and "13.2K" promoters therein are especially preferred.

The invention has particular relevance to poultry, especially chickens. For this purpose, any foreign gene relevant to improving the condition of poultry could be inserted into the fowlpox virus. Preferably the gene will be one appropriate to an in vivo sub-unit vaccine, for example one or more genes selected from Infectious Bronchitis Virus (IBV), Infectious Bursal Disease virus, Newcastle Disease Virus (NDV), Marek's disease virus, infectious laryngotracheitis virus and genes encoding antigenic proteins of Eimeria species. Particular genes of interest are the spike genes of IBV and the HN and F genes of NDV as described in PCT patent application publication No. WO 86/05806 and European Patent Application Publication No. 227414A (both National Research Development Corporation). In order for the foreign gene to be correctly translated in vivo it is necessary for the foreign gene to have its own ATG start codon inserted in the region just following the promoter.

More than one foreign gene can be expressed in a single poxvirus. It is possible to arrange for mRNA for two foreign genes to be transcribed in different directions when inserted in a single non-essential region. Such a "back to back" construction is shown in Example 7. Also, individual foreign genes can be inserted in individual NERs described herein. While fusion protein genes can, of course, be made, it is ordinarily preferable that each gene be under control of a separate promoter.

Figure 1:
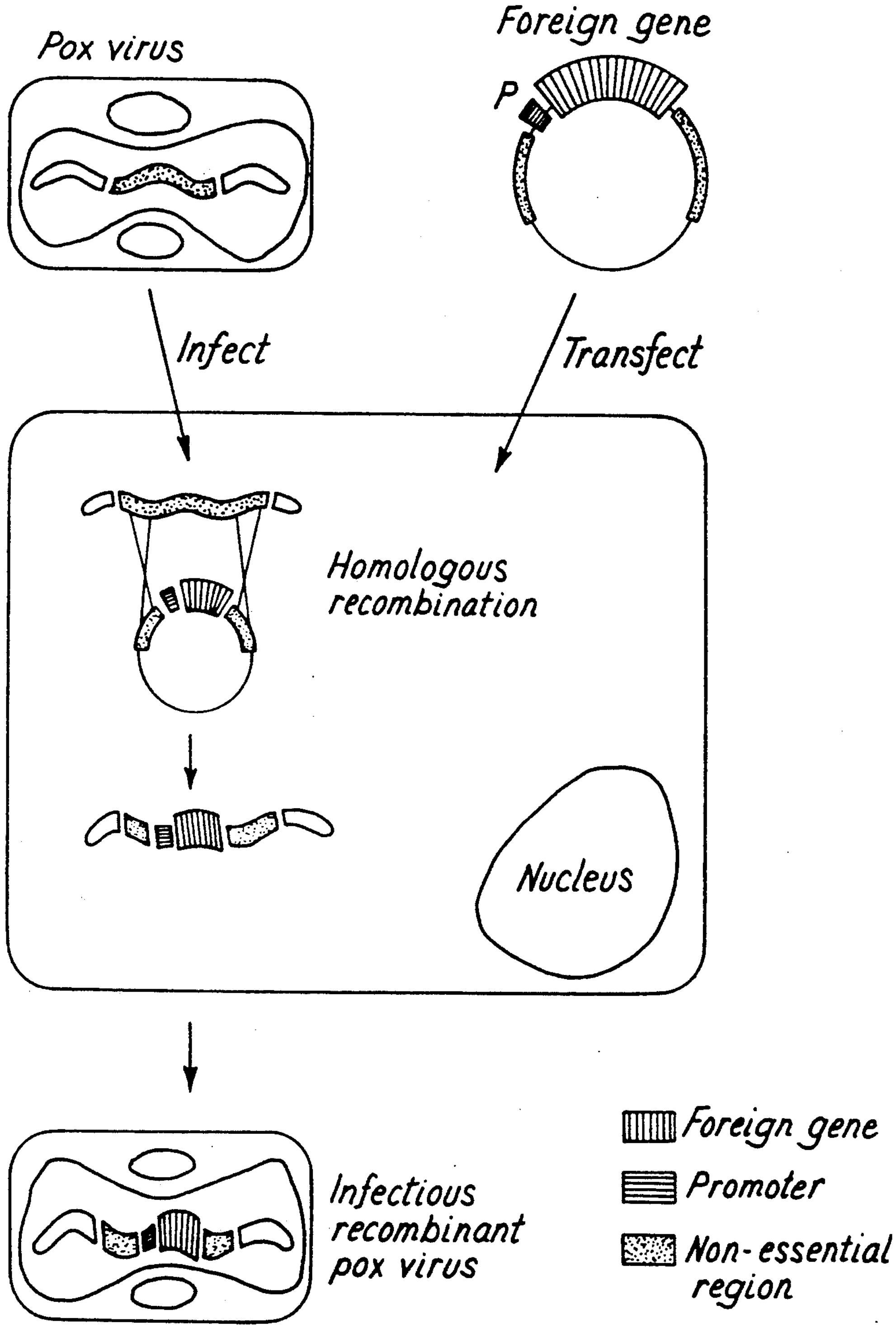
FIG. 1 is a schematic illustration of a homologous recombination process of the invention.

The promoter and foreign gene then have to be inserted into the non-essential region (NER) of the FPV genome. The procedure of homologous recombination, illustrated by FIG. 1 of the drawings, provides a way of doing so. A fragment of genomic DNA containing the NER is sub-cloned in a cloning vector. A construct is then made, in the cloning vector, comprising part of the NER followed by the promoter followed by the foreign gene, followed by a further part of the NER in the same orientation as the first part. This construct, in an appropriate vector, forms the recombination vector which is used to transfect the FPV, e.g. by the calcium phosphate method, whereby recombination occurs between the NER sequences in the recombination vector and the NER sequences in the FPV. The FPV then automatically re-packages this altered genome and the thus altered FPV (recombinant FPV) is part of this invention.

Figure 4:
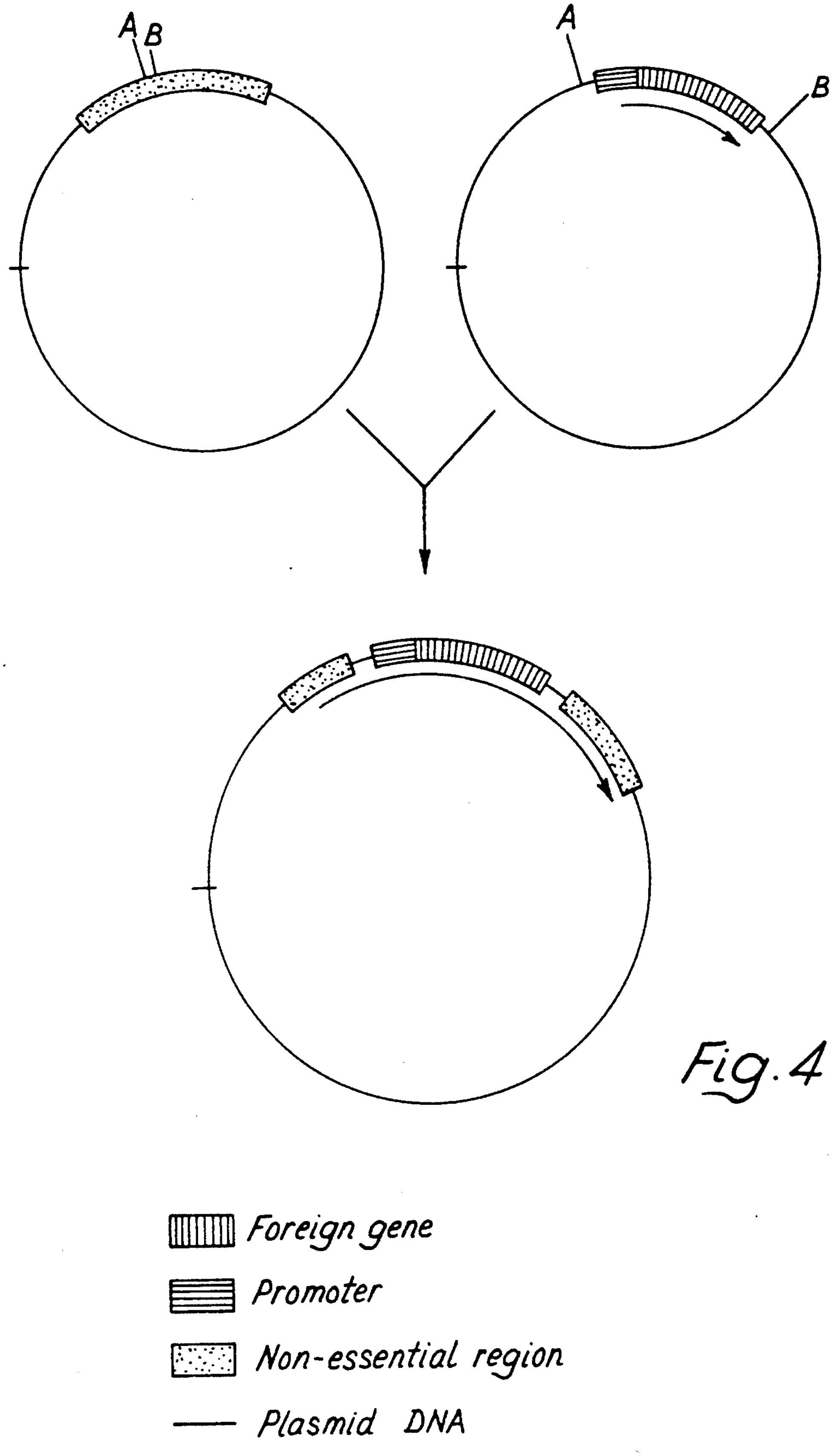

The above-described recombination vector can be prepared in many different ways, the requisite elements being introduced in any order. Referring to FIG. 4, a non-essential region defined above for use in the invention possessing (say) two restriction sites A, B is inserted in an appropriate vector, which by way of illustration only will be described as a plasmid. In another plasmid having the same (or ligatably compatible) restriction sites A, B, a construct is made of promoter sequence followed by the foreign gene sequence. It is of course essential that this construct is made so that the mRNA transcription will begin at or before the start codon of the foreign gene. Since it is time-consuming to determine precisely where the mRNA transcription start is effected by any particular promoter, it is convenient simply to insert, say, 100 or more preferably 150 base pairs of promoter DNA immediately preceding the FPV gene which it normally promotes, to ensure good working of the promoter.

The restriction sites A, B are located in the plasmid DNA flanking the FPV promoter DNA and the foreign gene. Of course, A can be within the promoter DNA if it falls within a non-functional portion thereof. While A and B can be two different restriction sites, they can, of course, be one and the same. They can be sticky- or blunt-ended sites and can be prepared artificially, e.g. by filling in with additional nucleotides or chewing back, in ways well known in the recombinant DNA field. Conveniently A and B are or are converted into a single blunt-ended site (C) and then allowed to ligate into a single blunt-ended site (C) within the NER. Care will have to be taken, of course, to select sites which are unique in the plasmid DNA to prevent ligation of other sequences of DNA from occurring. In the Example herein, unique sites for SpeI, NcoI and BglII in the NERs have been used and have been filled in to provide a single blunt-ended site for insertion of the promoter-gene construct.

DNA from the two plasmids are ligated together in vitro and then transformed into the host, to produce the final recombination plasmid of the invention.

Figure 5:
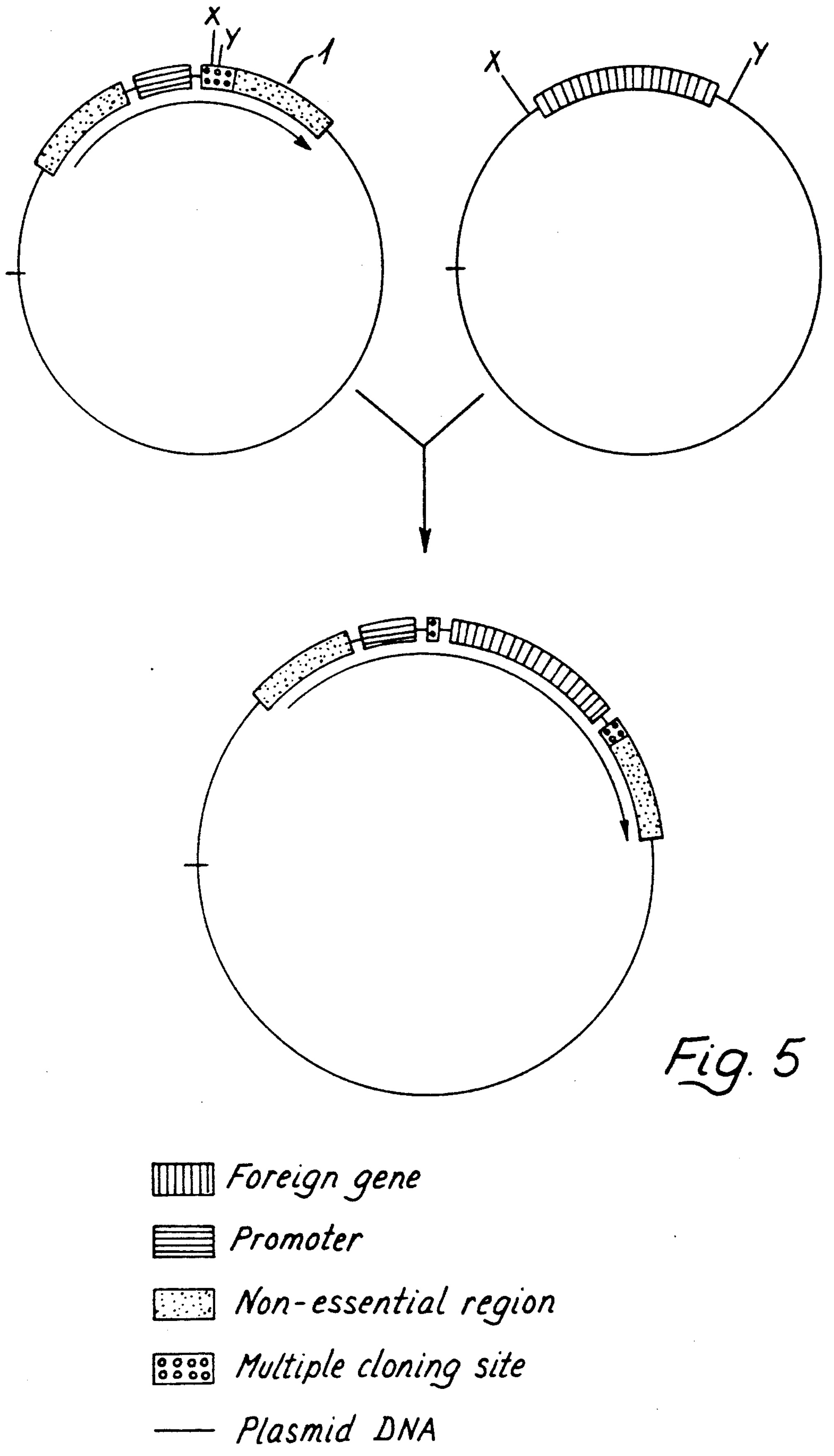

FIG. 5 illustrates another method of preparing recombinant vectors. In this method one first prepares a construct comprising a first part of the NER, followed by the promoter, followed by a short sequence of nucleotides containing at least one cloning site for introduction of a foreign gene, followed by a second part of the NER which will almost inevitably be in the same orientation as the first part. Of course, virtually any length of DNA would provide a cloning site suitable in some way or other for introducing a foreign gene. Preferably these constructs contain a multiple cloning site, that is to say a length of DNA containing the sites of a variety of different restriction enzymes, for example at least ten. Such a construct then has versatility, since it will then be much easier to restrict DNA flanking almost any foreign gene at sites close to each end thereof and insert the foreign gene into the multiple cloning site illustrated in FIG. 5. Only two sites X, Y have been shown, for simplicity and these can be filled in or chewed back, as desired, to give identical blunt-ended sites (Z, replacing X, Y). In the final recombination plasmids the promoter DNA will be separated from the foreign gene by a portion of the multiple cloning site, but this will not adversely affect the transcription of the MRNA in the final virus.

In either method of construction the NER is split by the promoter and foreign gene. It is, of course, not essential that it be split in a central region. Nor is it essential that the second part thereof constitute the entire balance or remainder of the NER. As explained above, so long as there exists within or at each end of the NER contains a long enough stretch of DNA for homologous recombination, it does not matter that a part of the NER might be excised somewhere in between or that additional (irrelevant) DNA be inserted in preparing the recombination plasmid, or even that the NER is only a few bp in length (but it should not normally be less than about 20 bp long or there would be practical difficulties in inserting the foreign DNA).

Figure 6:
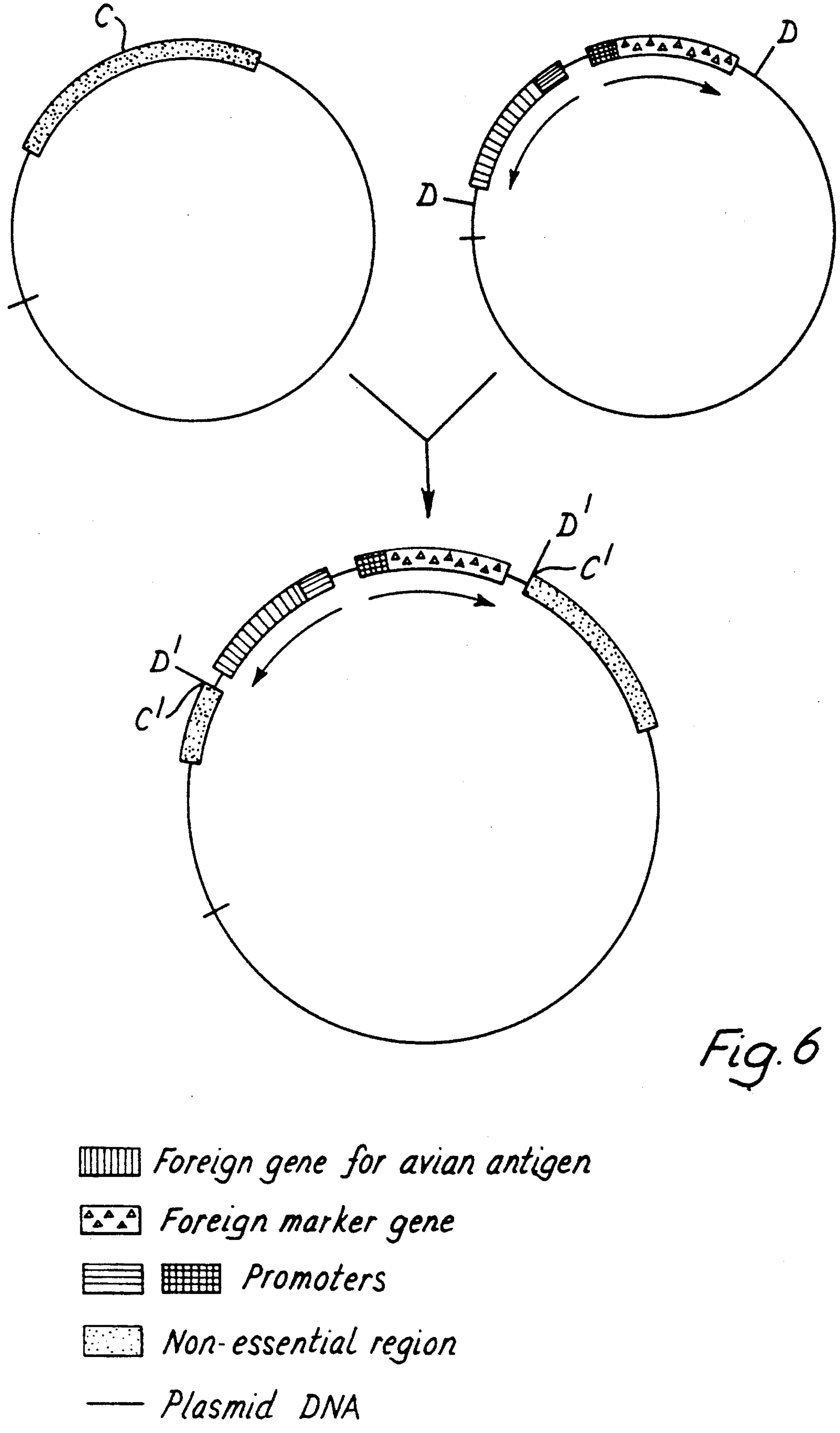

FIG. 6 illustrates another method of preparing a recombination plasmid. The NER plasmid is restricted as before (a blunt-ended site or sticky ended site filled in to become blunt-ended, C, is illustrated arbitrarily for this Figure). The other plasmid contains a marker gene with its own promoter and a foreign gene with its promoter in opposed orientations. Different promoters should be used to avoid the possibility of an incorrect recombination. When these plasmids are legated together the marker is linked to the foreign gene. The presence of the marker in the recombinant FPV is therefore likely to indicate a successful incorporation of the foreign gene into FPV. Conveniently the marker is readily detectable by a colour, fluorescent or chemiluminescent reaction. The beta-galactosidase or lacZ gene can be inserted into the NER and recombinants detected by the blue plaques generated when the 5-bromo-4-chloro-3-indolyl-D- galactopyranoside (X-gal) substrate is present in the growth medium. This technique, using the lacz gene, has been described in relation to VV by S. Chakrabarti et al., Molecular and Cellular Biology 5, 3403–3409 (1985).

Preferably the marker gene is also selectable (or it is replaced by a selectable gene or two separate genes, one marker and one selectable are included). An example of a selectable gene is the Ecogpt gene described in PCT Application WO 88/02022, already cited, and also by F. G. Falkner and B. Moss, J. Virology 62, 1849–1854 (1988).

It is also useful when preparing a recombination plasmid to know that the foreign gene is likely to have been successfully inserted into the NER. One way of checking is to adopt the procedure shown in FIG. 7. Again, blunt-ended sites (Z and W) are shown. In a first plasmid, containing the NER, a marker gene is inserted within the NER and optionally a multiple cloning site is inserted within the marker gene. The foreign gene with its promoter, contained in a separate plasmid, is then inserted into the marker gene by combining the two plasmids as shown. The foreign gene is inserted at any site within the marker gene which will interrupt or change its marker function, whereby the insertion can be recognised. For example, the *E. coli* lacZ gene can be used as the marker gene. Only the alpha-fragment need be inserted since the remaining elements of the gene required for processing are provided by the bacterial host. It is provided with the *E. coli* promoter for lacZ, the lacZ start codon and, preferably, a multiple cloning site within a few codons of the start, followed by sequence encoding the alpha fragment. When the alpha-fragment is interrupted by a foreign gene, conveniently insertable in the said multiple cloning site, the blue colonies given on an X-gal substrate are not ordinarily obtained. White colonies indicate a likely recombination plasmid.

The recombination vector could, on occasion, be further provided with a termination signal site to terminate transcription of mRNA, which might be useful for stabilising the mRNA when an early-acting promoter is used. This would be inserted downstream of the foreign gene. However, in many cases the ordinary termination signals of the infecting poxvirus or the signals for starting transcription of another, downstream, gene of the FPV will be adequate.

References herein to vectors other than FPV (or VV) mean any convenient prokaryotic or eukaryotic cloning vector appropriate for bulk production of the construct within a suitable host. Prokaryotic vectors will ordinarily be plasmids or phages. Suitable prokaryotic hosts include bacteria. Eukaryotic vectors such as those of fungi, yeasts and animal cells, e.g. SV40, can be employed if thought more convenient.

Although the recombination vector used will ordinarily be of double-stranded DNA, it is possible to use single-stranded DNA for the homologous recombination.

The recombination vector of the invention containing the NER, promoter and foreign gene then has to be "swapped over" for the "parent" FPV DNA. For this purpose, appropriate animal, preferably but not necessarily poultry, cells are infected with the parent FPV, and the recombination vector is then introduced into the cells. This process is carried out in vitro. It is best not to use wild type parent FPV for obvious reasons. FPV can readily be attenuated (mutated to make it less virulent), by any conventional method of attenuation.

Many different methods are available for detecting or selecting the recombinant viruses, and have been described for VV in a review article of M. Mackett and G. L. Smith, J. General Virology 67, 2067-2082 (1986). Such methods are applicable in the present invention. One method is to enlarge the recombination plasmid to include along with the desired foreign gene an additional marker gene as described above (FIG. 6). Alternatively, the insertion of the foreign gene can be detected by a hybridisation assay in which a labelled nucleotide sequence complementary to the foreign gene sequence is employed. Such assays are well known.

The FPV recombinants possessing the foreign gene are then grown in appropriate cells. The NER of the invention are non-essential in chicken embryo fibroblast cells. It would be necessary to carry out routine experiments to determine whether they are also usable for growth of FPV in other kinds of cell, e.g. chicken embryo skin cells, chicken fibroblasts, chicken embryo epithelial cells derived by conventional tissue culture methods, principally trypsinisation of tissues or the chorioallantoic membrane (CAM) of embryonated chicken or turkey eggs.

For administration to birds as a vaccine, the recombinant virus can be given to birds by any suitable method such as by aerosol, drinking water, oral, intramuscular injection or inoculation into the wing web. Ingredients such as skimmed milk or glycerol can be used to stabilise the virus. It is preferred to vaccinate chicks 1 day old by aerosol administration. A dose of from $10^2$ to $10^8$ pfu, preferably $10^4$ to $10^6$ pfu, of the recombinant FPV per bird is recommended in general.

While the invention is intended primarily for the treatment of chickens, it is potentially of interest in relation to the vaccination of other animals which might safely be inoculated with FPV. It is even possible that it might be considered safe to infect humans with FPV after appropriate trials have taken place.

The following Examples illustrate the invention.

EXAMPLE 1

This Example relates to terminal inverted repeat NERs.

Virus Strain

The HP438 strain of fowlpox virus was obtained from Professors A. Mayr and H. Mahnel, Ludwig-Maximillians University, Munich. The HP438 strain has been obtained from the pathogenic HP1 strain by 438 passages in chick embryo fibroblasts (CEFs) in tissue culture, A. Mayr et al., Zentralblatt fur Veterinarmedizin B13: 1-13 (1966). The HP 444 strain used to obtain DNA for cloning was derived by 6 further passages in CEF cells.

Tissue Culture Medium

CEF cells were grown in 199 (Wellcome) medium, supplemented with Penicillin (200 U/ml), Streptomycin (200 μg/ml), Fungizone (2 μg/ml) and 10% newborn calf serum.

Cell Culture and Viral DNA Purification

FPV strain HP444 was grown in primary chick embryo fibroblast (CEF) cultures and FPV DNA prepared as described by M. M. Binns et al., Nucleic Acids Research 15, 6563-6573 (1987).

Identification of the Terminal Fragment

The genome of poxviruses is double-stranded DNA. As usual the two strands are held together by hydrogen-bonding. However, at the ends of the genome of poxviruses the two strands are covalently linked. Topologically this means that the DNA is a continuous strand. When the genome is cut into fragments with a restriction enzyme, internal fragments are topologically different from terminal fragments and behave differently. On heating (to separate the two strands) the internal fragments completely separate and they reanneal slowly (hardly at all if one chills quickly). The terminal fragments, being covalently bonded, cannot separate very far spatially. On cooling they reanneal quickly by starting at the middle and "zipping up". This is called 'snap-back'. After heating and rapid cooling therefore, only the terminal fragments can be seen by gel electrophoresis. This method of identification of the terminal fragment, called "the snap back method," see L. C. Archard & M. Mackett, J. General Virol, 45, 61-63 (1979), was used here.

A BamHI restriction digest (10 μg) DNA was extracted once with phenol, the aqueous phase was extracted with diethyl ether to remove phenol and the DNA in the aqueous phase was precipitated with ethanol. The DNA pellet was dried and resuspended in 20 μl of TE (10 mM Tris HCl pH 7.5, 1 mM, EDTA). The DNA solution (10 μl) was then denatured by the addition of 40 μl of 95% v/v deionized formamide in 50 mM Tris HCl pH 7.5 and incubated at 60° C. for 10 minutes.

The sample tube was then rapidly cooled on wet ice containing NaCl for 10 minutes before analysing the DNA by agarose gel electrophoresis. The presumed terminal fragment renatured rapidly only in the native FPV DNA and was detected as an approximately 6.3 kb band. There is only one BamHI—derived snap back fragment, as the BamHI site falls well within the TIRs.

Cloning of the End Fragment of FPV DNA

The terminal crosslinks of the BamHI fragment were digested with S1 nuclease; using 100 μg of FPV DNA and 20 units S1 nuclease (Boehringer Mannheim) in 250 μl of 30 mM sodium acetate, pH 4.5; 0.3M NaCl; 1 mM $ZNSO_4$; 5% (v/v) glycerol at 37° C. for 20 minutes. To end-repair the DNA, it was then ethanol-precipitated and re-suspended in 100 μl of legation buffer (50 mM Tris. HCl pH 7.5, 10 mM magnesium chloride, 10 mM DTT) containing 5 units of *E. coli* polymerase I Klenow fragment and 1 unit of $T_4$ DNA polymerase and 0.025 mM each of dATP, dCTP, dGTP, and dTTP. This reaction was left for 1 hour at room temperature. It was stopped by heating for 10 minutes at 70° C. and 20 μl thereof was digested with 10 units of BamHI (Boehringer Mannheim) in accordance with the manufacturer's recommendations. 5 μl of this DNA was ligated to 20 ng of BamHI/Sma I—cut plasmid pBGS19, B. G. Spratt et al., Gene 41, 337-342 (1986), to make a total volume of 20 μl ligation buffer containing 2 units of $T_4$ DNA ligase and 1 mM ATP, and incubated at 4° C. overnight and transformed into *E. coli*. Screening for recombinants which contained the end fragment was carried out with a radiolabelled FPV BamHI terminal fragment isolated from a gel, using standard procedures as described by T. Maniatis et al. "Molecular Cloning: A Laboratory Manual", New York, Cold Spring Harbor Laboratory (1982) and Holmes and Quigley, Analytical Biochemistry 114, 193-197. A recombinant plasmid pB3 was isolated.

Cloning of NERs

Figure 8:
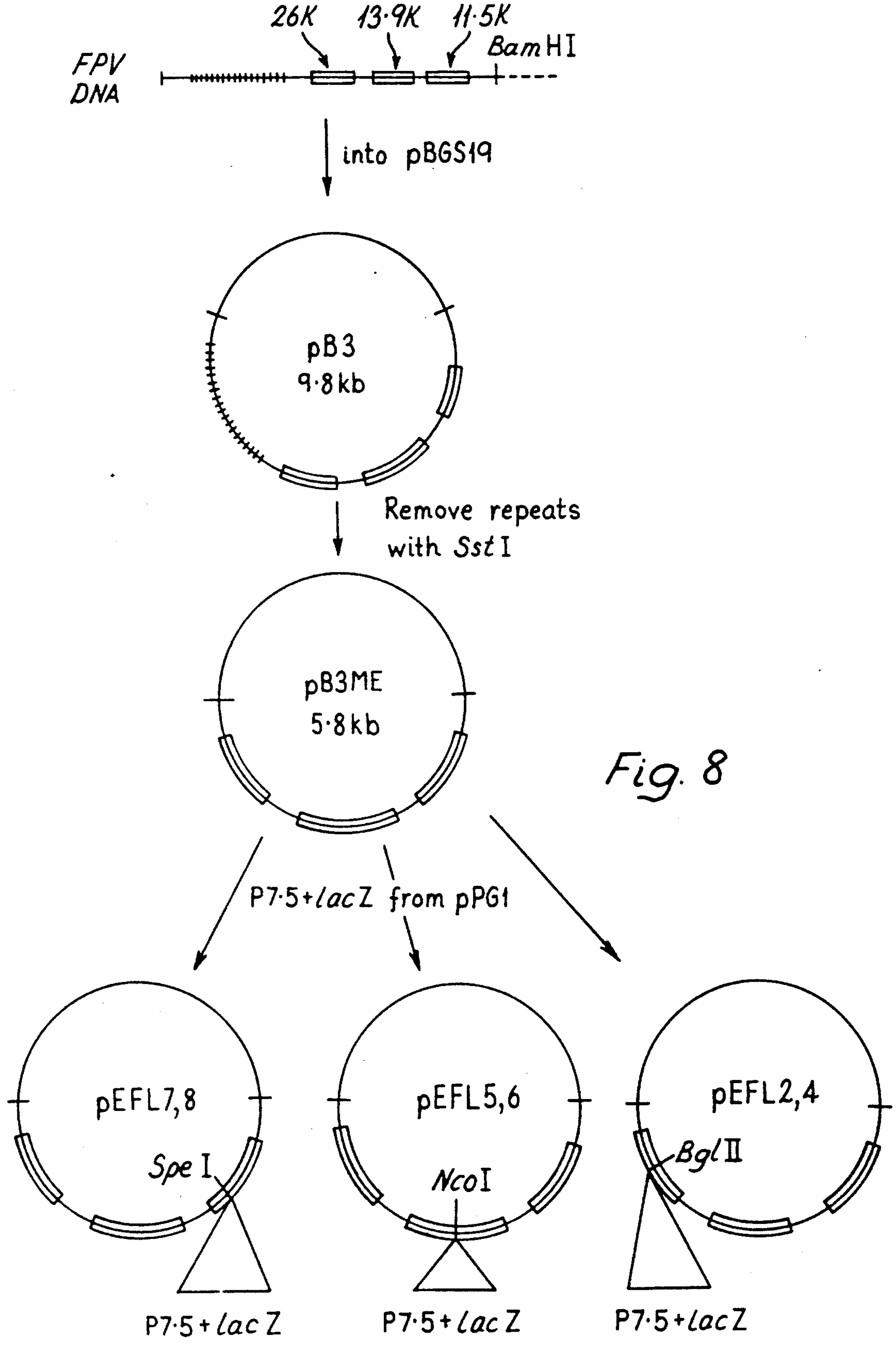
FIG. 8 illustrates schematically the construction of specific recombination plasmids of the invention containing non-essential region sequence of FPV into which a foreign gene is inserted.

The three genes under test for non-essentiality were retained together in their natural sequence in a shortened modification of plasmid pB3, see FIG. 8. pB3 was shortened by removing the short unique sequence and the repeated sequences (see FIG. 8) from the BamHI fragment. This was done by a digestion with SstI There is a SstI site in pBGS19 just before the BamHI site into which the FPV BamHI fragment was inserted. The SstI digestion was carried out at 37° C. in a total of 20 μl of the recommended buffer, using 10 units of SstI. There are many SstI sites in the repeated sequence, the last of which causes cutting at nucleotide 4005. Thus, after cutting with SstI, the plasmid pB3 (9.8 kb) was religated in a 100 μl volume, to favor intramolecular ligation using the previously described ligation buffer, at 15° C. overnight, to produce plasmid pB3ME (5.8 kb) which lacks 4.0 kb of the BamHI fragment DNA. To select the 5.8 kb clones, rather than those which have lost shorter lengths of SstI- cut DNA, selected colonies were grown up and then subjected to gel electrophoresis. To check that all the repeats were removed, the plasmid was digested with BglII and the fragments analysed by gel electrophoresis.

Preparation of a Plasmid Containing the VV 7.5K Promoter and the lacZ Gene

The VV 7.5K promoter is available in a plasmid pGS20 from Dr. Geoff Smith, Division of Virology, Dept. of Pathology, University of Cambridge, Addenbrooke's Site, Hills Road, Cambridge, England. Cambridge and is described in M. Mackett, G. L. Smith and B. Moss J. Virology 49, 857-864 (1984) and can be combined with *E. coli*. lacZ sequences as shown in the DNA sequence below. The resultant plasmid is designated pPGl. Other methods which could be used to combine the VV 7.5K promoter and lacZ sequence have been described in papers relating to VV.

p7.5 sequences from pGS20
1 GGATCCCCAATTCCAGCTTGGCTGCAGGTCGACATATACTATATAGTAATACCAATACTC

61 AAGACTACGAAACTGATACAATCTCTTATCATGTGGGTAATGTTCTCGATGTCGAATAGC

121 CATATGCCGGTAGTTGCGATATACATAAACTGATCACTAATTCCAAACCCACCCGCTTTT

181 TATAGTAAGTTTTTCACCCATAAATAATAAATACAATAATTAATTTCTCGTAAAAGTAGA p7.5 sequences from pGS20
241 AAATATATTCTAATTTATTGCACGGTAAGGAAGTAGAATCATAAAGAACGTGACGGATCG SV40 sequences + linking DNA sequences | lacZ sequences
301 AAGCTTTGCAAAGATGGATAAAGTTTTCCGGAATTCCAAGCTTGGCCTGGCCGTCGTTTT
Met Asp Lys Val Phe Arg Asn Ser Lys Leu Gly Leu Ala Val Val Leu 361 ACAACGTCGTGACTGGGAAAACCCTGGCGTTACCCAACTTAATCGCCTTGCAGCACATCC
Gln Arg Arg Asp Trp Glu Asn Pro Gly Val Thr Gln Leu Asn Arg Leu Ala Ala His Pro . . . . . . . . . . continuation of lacZ sequences . . . . . . . . . .

3301 GGGGATTGGTGGCGACGACTCCTGGAGCCCGTCAGTATCGGCGGAATTCCAGCTGAGCGC
Gly Ile Gly Gly Asp Asp Ser Trp Ser Pro Ser Val Ser Ala Glu Phe Gln Leu Ser Ala

-continued

```
-------- lacZ sequences ------------------------------------------------------>< ---------linking
3361 CGGTCGCTACCATTACCAGTTGGTCTGGTGTCAAAAATAATAATAACCGGGCAGGGGGGA
     Gly  Arg  Tyr  His  Tyr  Gln  Leu  Val  Trp  Cys  Gln  Lys  ***

sequences ---->< ----SV40 sequences -----------------------------------------
3421 TCTGAACTTGTTTATTGCAGCTTATAATGGTTACAAATAAAGCAATAGCATCACAAATTT

     ------------------------------------------------------------------------
3481 CACAAATAAAGCATTTTTTTCACTGCATTCTAGTTGTGGTTTGTCCAAACTCATCAATGT

     --SV40 sequences ---------->
3541 ATCTTATCATGTCTGGATCGGGGATCC
```

Insertion of the VV 7.5K Promoter/lacZ Gene Construct into FPV NERs to Make Recombination Plasmids The P7.5+lacZ fragment (about 3.6 kb) in 2 μl total volume of buffer was cut out of the ampicillin—resistant plasmid pPGl with 10 units of BamHI. The ends of the DNA were then repaired with the Klenow fragment of DNA polymerase to produce blunt-ended DNA molecules. Thus, the fragment was phenol-extracted with an equal volume of TE- saturated phenol and ethanol- precipitated. It was resuspended in 20 μl of ligation buffer containing 5 units of Klenow fragment in 1 unit of $T_4$ polymerase, containing 0.025 mM of each of dATP, dCTP, dTTP and dGTP and stood for 1 hour at room temperature. Similarly, the pB3ME (SpeI, NcoI and BglII) were also digested with BamII and repaired to produce blunt-ended sites. The P7.5+lacZ fragment was then blunt-end ligated into pB3ME as follows. Thus, the plasmid and fragment (20 ng each) were ligated in a total volume of 10 μl above described ligation buffer containing 1 unit of $T_4$ DNA ligase and 1 mM ATP and incubated at 4° C. overnight and were transformed into *E. coli*. Blue colonies of X-gal Kanamycin plates were selected (PBGS 19 is a Kanamycin-resistant vector) and the DNA of several colonies was examined by the method of Holmes and Quigley, loc. cit. Each ligation produced two different results, i.e. the P7.5+lacZ could be ligated into pB3ME in either of two different orientations. The pairs of constructs of each site were called pEFL2/4, pEFL5/6 and pEFL7/8. In pEFL, 2, 6 and 8, the P7.5+lacZ insert was in the same orientation as the gene into which it was inserted i.e. left to right in pEFL2 (BglII, 26.0) and pEFL8 (SpeI, 11.5) and right to left in pEFL6 (NcoI, 13.9).

Recombination

The plasmids PEFL 2, 6 and 8 which contained the P7.5K promoter/lacz construct in the orientations described were used in recombination experiments. The recombination has the following general stages:

1. Infect CEF cells with FPV, and add the recombination plasmid DNA in the form of a pre-prepared calcium phosphate precipitate. Allow to grow for several days. (Recombination takes place)
2. Harvest cells and freeze-thaw three times (Virus is released from cells).
3. Add this preparation to CEFs at various dilutions to produce plates with about 500–1000 plaques per 10 cm dish (about 0.1% of these are recombinant plaques).
4. Add Xgal overlay and visualise blue plaques.
5. Pick isolated plaques. Freeze-thaw three times to release virus from cells of plaque.
6. Titrate again on CEFs and get more plaques.
7. Loop back to 4, repeating stages 4–6, until a pure plaque of the recombinant is obtained.

In more detail, chick embryo fibroblast cells, when about 80% confluent, were infected with about 3 plaque forming units (infectious virus particles) per cell of plaque-purified HP 440. fowlpoxvirus. The virus was contained in 1 ml of commercially available serum free medium ("199"), and was left to adsorb to the cells for 2 hours at 37° C., after which the virus inoculum was removed and 10 ml of fresh medium containing 5% newborn calf serum (CS) was added. 1.5 hours later a precipitate of the plasmid DNA construct to be recombined into the virus was prepared: to 1 ml of Hepes-buffered saline (pH7.12) was added 10–20 μg of the pEFL 2, 6 or 8 plasmid DNA in solution in TE at about 1 μg/μl. 50 μl of 2.5M calcium chloride was added slowly, and a fine DNA/calcium phosphate precipitate was allowed to form for 30 minutes at room temperature (25° C.). The medium from the virus-infected cells was then removed, the 1 ml of precipitate was added to the cells and left for 30 minutes at room temperature. Then 10 ml of fresh medium containing 5% CS was added to the cells, and they were incubated at 37° C. for a further 4 hours. The condition of the cells was then examined and if the DNA calcium phosphate precipitate was considered too thick, the medium was replaced. Otherwise it was then replaced the next day. The cells were incubated at 37° C. for a further 5 days and then the virus was harvested by scraping the cells into the medium. Intracellular virus was released by three cycles of freeze-thawing and the virus titrated by a conventional plaque titration.

The liquid medium was removed from the cells and an overlay of cell culture medium in 1% low gelling temperature agarose (LGT) containing 300 μg/ml (5-bromo-4-chloro-3-indolylbeta D-galactoside) was added. After overnight incubation at 37° C., plaques expressing the lacZ gene, blue in colour, were observed.

Blue plaques were picked into 500 μl of 10 mM Tris pH9, intracellular virus was released by three cycles of freeze-thawing and the virus titrated by a conventional plaque titration. The process of picking plaques and re-titrating was repeated until a plaque purified recombinant was obtained.

The plaque-purified recombinants were then passaged in tissue culture for the following numbers of passages after the first picking:

recombinants from plasmid pEFL 8 (SpeI insertion): stable for at least 3 passages -continued

| |
|---|
| 6 (NcoI insertion): stable for only 2 passages |
| 2 (BglII insertion): stable for at least 6 passages. |

It is possible that the NcoI-based recombinants might be stable for a longer period under different conditions from those tried above.

DNA Analysis of FPV Recombinants

When the DNA of the FPV parent is digested with BamHI a number of restriction fragments are generated, which can be separated on agarose gels. The terminal fragment is of size 6.3 kb and is of double intensity compared with the other bands since there are two copies of it (one from each end of the genome). When the DNA of the recombinant made with pEFL2 was digested the pattern of bands was the same except that the double 6.3 kb fragment had been replaced by a double 9.9 kb fragment. This is consistent with the increase in size from 6.3 kb to 9.9 kb which would be produced if the 3.6 kb P7.5+lacZ fragment had been inserted into the terminal fragment. Probing of the restriction digest after transfer to nitrocellulose showed that the 9.9 kb band did in fact contain lacZ sequences.

EXAMPLE 2

This Example relates to D8–D9 NERs.

In order to test whether D9, D10 and the fowlpox gene present in the D8 position were non-essential for growth further manipulations were carried out.

1. For D8 the plasmid pMB389 was grown in a dam− *E. coli* host WK262 and reisolated as pMB434. The reason for this is that in the usual strains of *E. coli,* the enzyme BclI to be used here cannot restrict because its control adenine base in its TGATCA recognition sequence is methylated. The dam− strain resists methylation and in this host the enzyme BclI would be able to cleave its two recognition sites which occurred in the D8 region. This plasmid was then cleaved with BclI and religated and a clone from which the 583 bp BclI fragment was missing was isolated by screening a number of colonies with small plasmid preps. Such a plasmid pMB441 containing a unique BclI site and having much of its D8 region removed was isolated. A BamHI fragment from pBPGl, containing the β-galactosidase gene, under the control of the vaccinia P7.5K promoter, was then inserted into this unique BclI site of pMB441 (BamHI and BclI generate compatible sticky ends such that no end-repairing was necessary). A plasmid clone pMB447 containing the correct structure was isolated and used in recombination assays (see later).

2. For D9 pMB389 was cleaved with AsuII (a unique site for which exists in the D9 gene) and end-repaired. pBPGl was cleaved with BamHI and end-repaired and then ligated with AsuII cleaved pMB389 which had also been end-repaired. One colony selected as blue on Xgal Amp plates was found to contain the vaccinia P7.5K promoter and β-galactosidase gene inserted in the D9 gene.

3. For D10 an EcoRI fragment was subcloned from pMB389 (one EcoRI site lies within the D9 gene whilst the other is in the polylinker of the pUC13 vector of pMB389) into pUC13 cut with EcoRI. The resulting plasmid pMB439 contains a unique BUIII site within the DIO gene. The BamHI fragment containing the vaccinia P7.5K promoter and the β-galactosidase gene were cloned into the BglII site of pMB439 to generate pMB443. (Again no end-repair was necessary as BamHI and BglII also have compatible sticky ends). Plasmed pMB443 was then tested in recombination assays.

Figure 10:
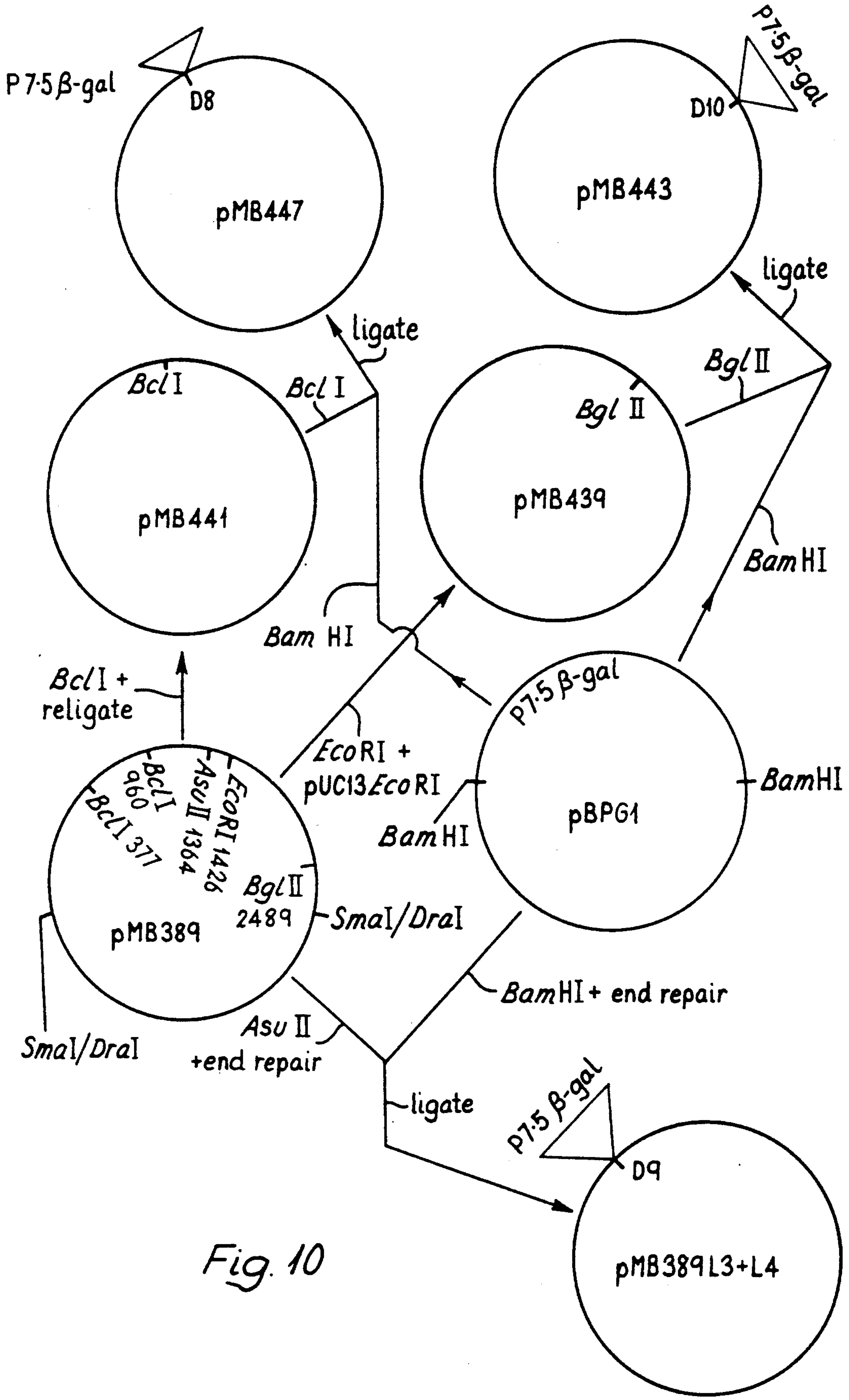
FIG. 10 illustrates schematically the construction of specific recombination plasmids of the invention containing sequence within the D8, D9 and D10 genes (D8, D9 according to the invention; D10 comparative) into which a foreign gene is inserted.

The plasmid constructions described above are illustrated schematically in FIG. 10. The plasmid pBGI is derived by cutting the BamHI fragment from pPGI, this fragment containing the P7.5-β-galactosidase gene construct, and inserting it in the plasmid pBGS19 (refer to Example 1).

Recombination

Viruses from initial blue plaques from a recombination experiment were plaque-purified three times and appeared stable (i.e. no white plaques were observed on the third passage). Viral DNA was made from the plaque-purified viruses, and digested with EcoRI. DNA from the original (non-recombinant) ("wild type") FPV was also digested with EcoRI to serve as a control. The DNAs were run on duplicate agarose gels, Southern blotted, and probed with either the putatively recombinant FPV EcoRI fragment, within which the insertions should have taken place, or with pPGl containing the β-galactosidase gene. Comparing the putatively recombinant FPV with the wild type when the EcoRI digests were run on gels, the normal EcoRI fragment present in wild-type DNA had increased in size in both the D8 and D9 putative recombinants. The new D8 fragment was smaller than the new D9 one, as expected, due to the removal of the small BclI fragment (377–960) in this case. When probed with β-galactosidase gene-containing pBGl plasmid DNA, wild-type FPV DNA did not light up but the D8 and D9 putative recombinants both lit up in the same positions as when the probe from the putatively recombinant EcoRI fragment was used. This established that the structures of the D8 and D9 recombinants were as expected.

Similar experiments for the D10 gene failed to give the desired confirmations.

EXAMPLE 3

Virus Strain

This Example describes the construction of vectors containing Newcastle Disease Virus (NDV) F and HN genes, successful protection of birds using the F. gene. TIR NERs were used.

A. Subcloning of NDV Fusion (F) and Haemagglutinin-Neuraminidase (HN) Genes

Figure 11:
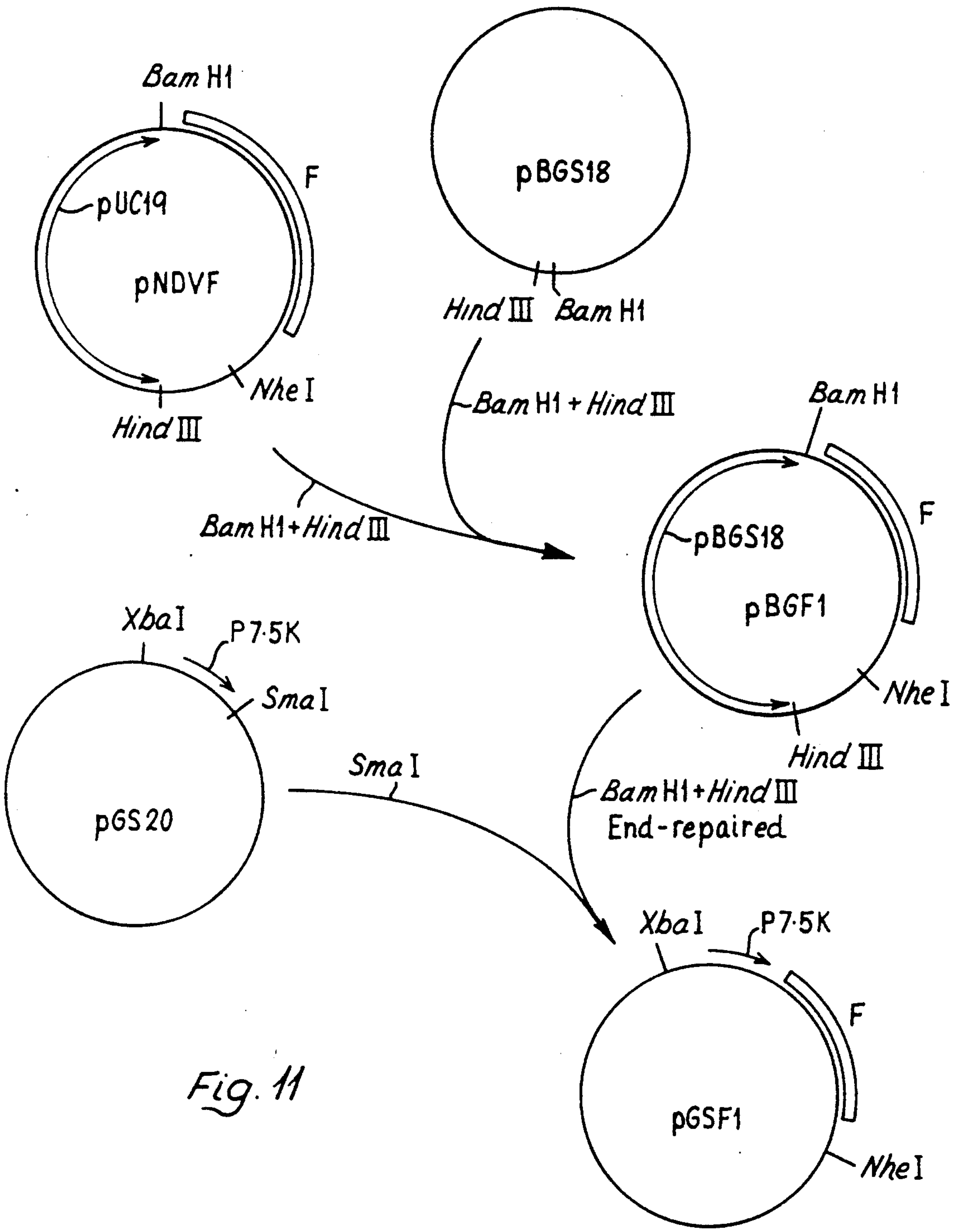
FIG. 11 depicts construction of plasmid pBGF1.

The F and HN genes of NDV were provided as a gift from Professor P. T. Emmerson of the University of Newcastle-upon-Tyne, each cloned into the plasmid pUC19, P. Chambers et al., Journal of General Virology, 67, 2685–2694 (1986); N. S. Millar et al., Journal of General Virology, 67, 1917–1927 (1986). See also European Patent Application 227414 (National Research Development Corporation) which refers to Budapest Treaty patent deposits of NDV cDNA in plasmids pUC18, and pUC19 at the National Collection of Industrial Bacteria, Aberdeen, Scotland on 1st July 1986 as NCIB 12277 (F gene) and 12278 (HN gene). Referring to the pUC19 clones actually used herein, the F gene clone also contained part of the HN gene downstream thereof. The F gene was subcloned by cutting with the restriction enzyme BamHI (which conveniently cuts 29 bases upstream of the initiating ATG codon at the 5′ end of the F gene) and HindIII (which cuts approximately 820 bases downstream from the 3' end of the F gene, this extra sequence including some of the HN gene) into the kanamycin-resistant plasmid pBGS18 cut with BamHI and HindIII. The resulting plasmid was called pBGFl (see FIG. 11).

The pUC19 μlasmid containing the HN gene also has F gene sequence upstream of the HN gene. In order to facilitate positioning of a poxvirus promoter adjacent to the HN gene, the F gene sequences were removed by the use of the exonuclease Bal31. The plasmid was cleaved with the restriction enzyme SphI (which cuts in the multiple cloning site of pUC19 on the 5' side of the HN gene) and digested for a range of appropriate times as follows. The method used was as described in "Molecular Cloning (A Laboratory Manual)" by T. Maniatis et al., Cold Spring Harbor USA (1982). 20 μl of DNA (at approximately 500 μg/ml) were mixed with 20 μl BSA (1 mg/ml) and 40 μl of 2×"Bal31 buffer" (24 mM $CaCl_2$, 24 mM $MgCl_2$, 0.4M NaCl, 40 mM Tris/HCl pH 8.0, 2 mM EDTA) and warmed to 30° C. 0.5 unit of Bal31 was added and samples were incubated for 0, 1, 2, 3, 4 and 5 minutes. Then 20 μl of water and 3 μl of 0.5M Tris/HCl pH 7.5, 100 mM $MgCl_2$ were added, and the samples were digested with 10 units of SstI (which cuts downstream of the HN gene) for 60 minutes. Samples were run on an agarose gel to estimate the amount of DNA digested, and the 0, 1 and 2 minute samples were chosen for further use. The molecules were then repaired (as described above) with T4 DNA polymerase and Klenow fragment and cloned into SmaI-cut pBGS18. Several different isolates were sequenced at the 5' end of the HN gene and one was found in which only 49 of the bases upstream of the gene remained (starting at the sequence GGCTTCACAA . . . ). This plasmid was called pBHNl (see FIG. 13).

B. Cloning of the F Gene into a Recombination Vector

Figure 12:
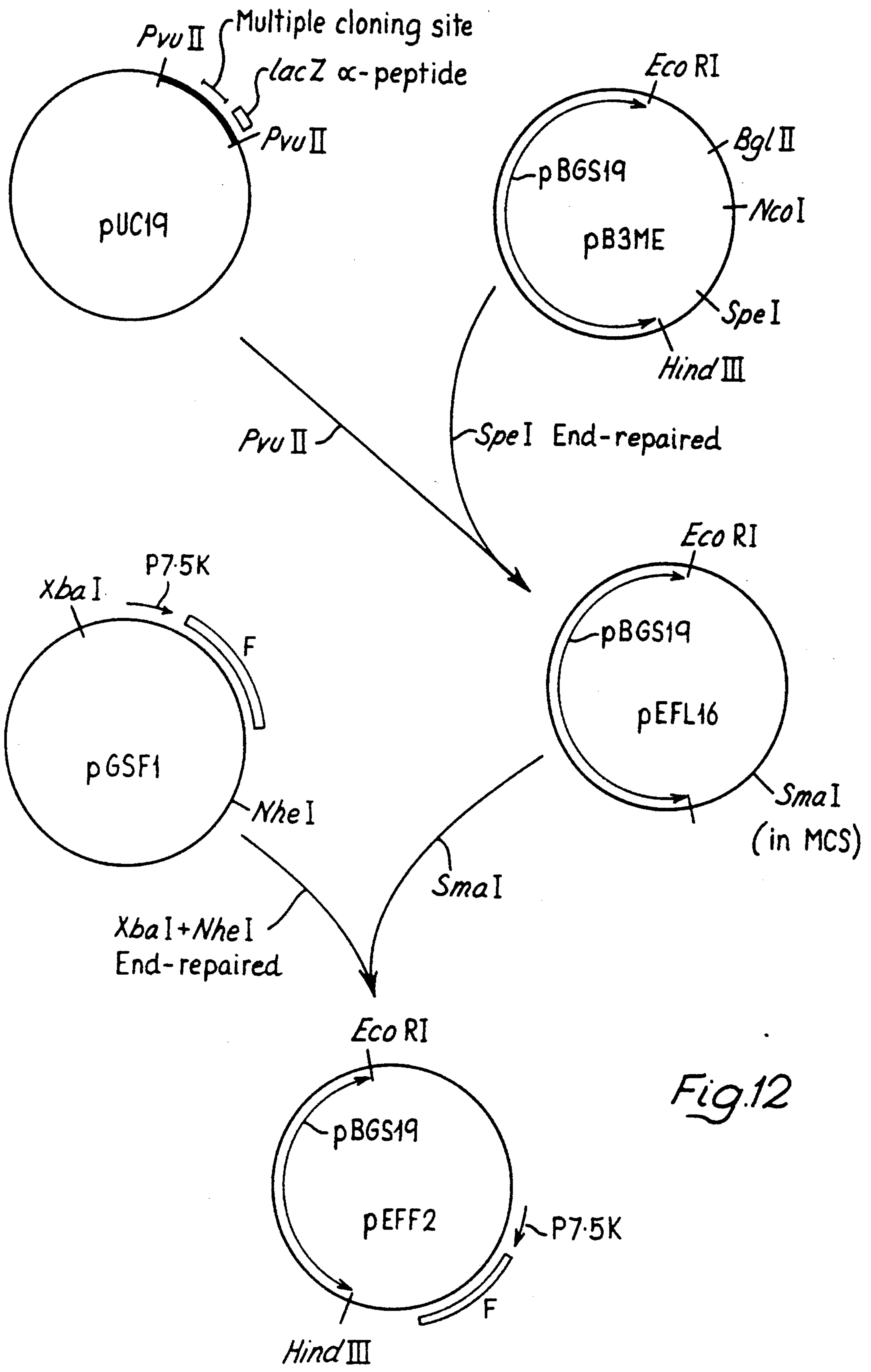
FIG. 12 depicts construction of plasmid pEFF2.

In order to place the F gene under the control of the P7.5K VV promoter, the F gene was excised from pBGFl with BamHI and HindIII, end-repaired as described, and cloned into the Smai site of pGS20 (Mackett et al., Journal of Virology 49, 857-864). This plasmid was called pGSFl (see FIG. 11). A plasmid pEFL16 (FIG. 12) was constructed by inserting the PvuII fragment from pUC19 into the SpeI site of pB3ME (described above). This fragment contains the coding sequences of the alpha peptide of beta-galactosidase with a multiple cloning site arranged such that when fragments are cloned into this site the translation of the beta-galactosidase is disrupted and thus recombinants can be detected because they are white colonies on plates containing Xgal. (This construct pEFL16 is now equivalent to the 'recombination plasmid' described in Example 1 and shown in FIG. 7). The F gene plus P7.5 promoter was excised from pGSFl by using XbaI and NheI, end-repaired as described, and cloned into the unique SmaI site of pEF16. The resulting plasmid (which now has the F gene, with the P7.5 promoter upstream, placed within the SpeI non-essential region of the terminal fragment of fowlpox) is called pEFF2 (FIG. 12).

C. Cloning of the HN Gene into a Recombination Vector

Figure 13:
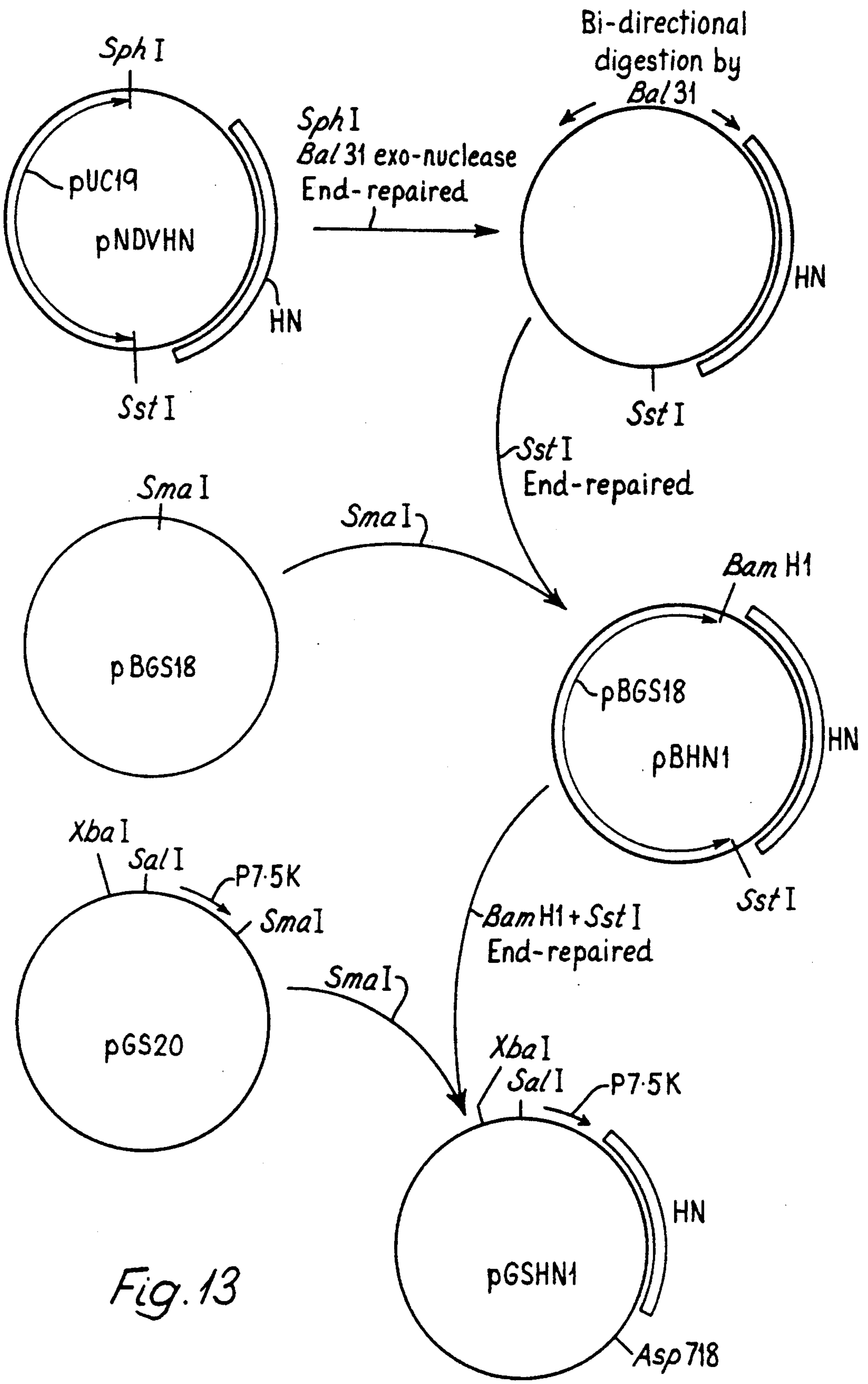
FIG. 13 depicts construction of plasmid pBHN1.
Figure 14:
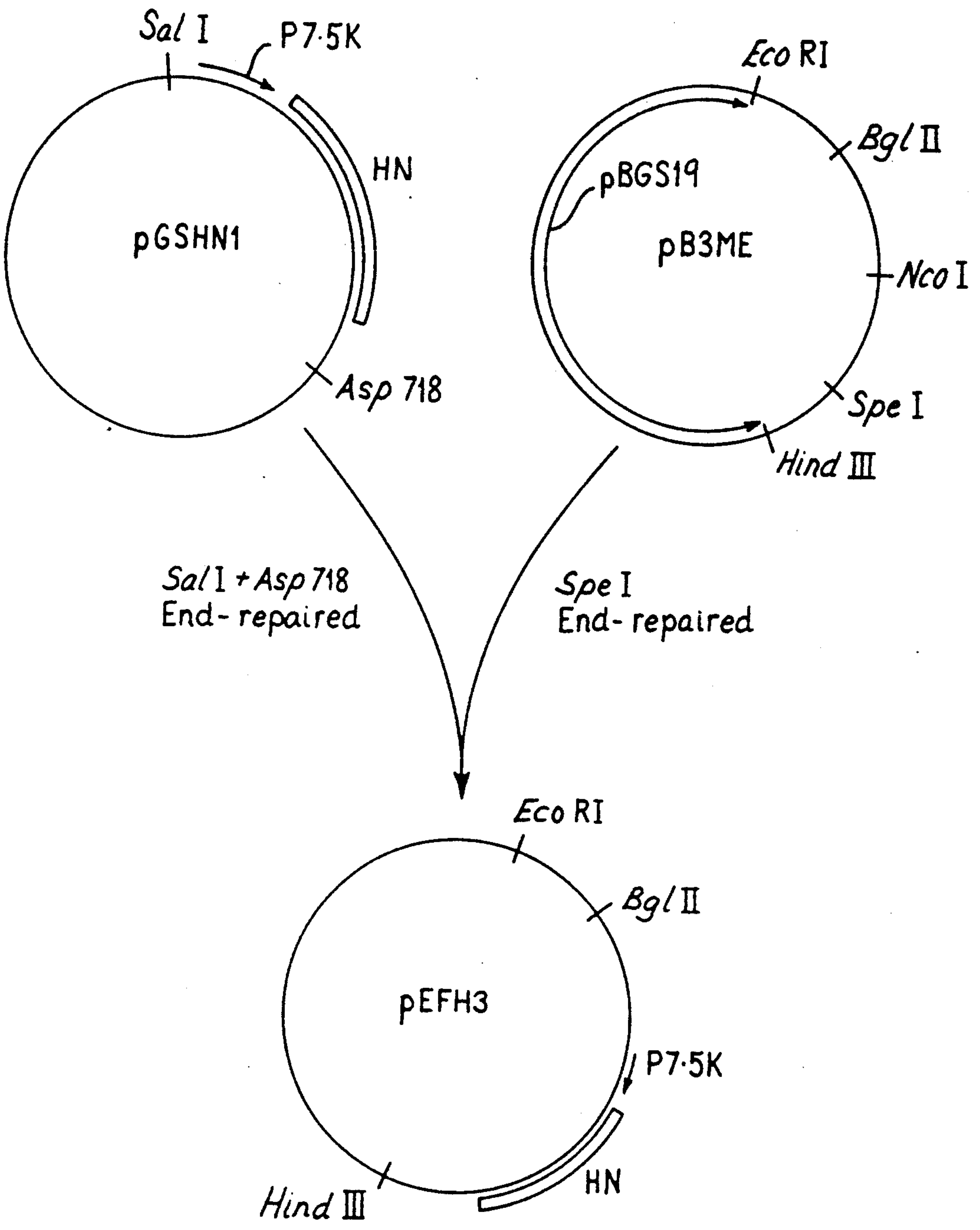
FIG. 14 depicts construction of plasmid pEFH3.

In order to place the HN gene under the control of the P7.5 promoter it was excised from pBHNl with SstI and BamHI, repaired as described, and cloned into the SmaI site of pGS20. This plasmid was called pGSHNl (FIG. 13). The HN gene plus P7.5 promoter was excised from pGSHNl by using SalI and Asp718, repaired as described, and cloned into pB3ME which had been cut with SpeI and repaired. This plasmid was called pEFH3 (see FIG. 14).

D. Production of FPV Recombinant Containing the F Gene

The Poxine strain of fowlpox virus used was kindly donated by Duphar. It was passaged three times in chicken embryo fibroblast cells CEFs in tissue culture. A single plaque was picked at this stage and was plaque-purified three times. The virus thus obtained was called Px4.1. and was grown in tissue culture as described for the HP444 strain in Example 1.

The plasmid pEFF2 was allowed to recombine into the Px4.1 strain of FPV, as described in Example 1. The virus from the recombinations was titrated on CEFs and then plaqued out on 10 cm petri dishes at a concentration of virus producing about 1000 plaques per dish. The virus was overlaid with cell culture medium in 1% low gelling temperature agarose. After 4-5 days the agarose overlay was removed and stored at 4° C. in a sterile petri dish. A dry nitrocellulose filter was laid onto the cell sheet and pressed down with a circle of Whatman 3 MM chromatography paper soaked in 20 X SSC. The filter was then lifted off the dish, with the cell sheet and plaques adhered to it, the 3MMs paper removed, and the filter was baked at 80° C. in a vacuum for 2 hours. To identify recombinant viruses, the filters were then probed with radiolabelled probes specific for either the F gene or the HN gene. The filters were exposed to X-ray film and the position of recombinant plaques identified by aligning the autoradiograms with the stored agarose overlays. Recombinant virus was then isolated from the agarose overlay by removing a plug of agarose using a pasteur pipette. This plug was resuspended in 10 mM Tris pH 9.0, freeze-thawed three times and replaqued. Recombinant virus was identified again by probing, and this process was repeated three times in all until a plaque-purified virus was achieved.

E. Production of FPV Recombinant Containing the HN Gene

The plasmid pEFH3 was allowed to recombine, as described above, into the plaque-purified HP440 virus (HP 438 as described in Example 1, plus two further passages). This virus is called FP9. Recombinant virus containing the HN gene was isolated as described for the F gene.

F. Expression of the F Gene in Tissue Culture

The recombinant viruses, and the equivalent parent strain as controls, were used to infect 5 cm petri dishes of CEFs at approximately 5 pfu/cell. The virus was allowed to grow for various times and then the cells lysed by addition of 500μl of boiling sample buffer (containing 24 mM Tris/HCl PH 6.8, 1% SDS, 20% glycerol and 0.02% bromophenol blue). For the HN recombinant this buffer also included 0.1M dithiothreitol. The infected cells were scraped into the sample buffer, and the samples boiled for 2 minutes, cooled on ice, and frozen at −20° C. Samples were then loaded onto standard polyacrylamide protein gels, electrophoresed to separate the proteins, and transferred to nitrocellulose filters by Western blotting. The Western blots were probed (as described in A. C. R. Samson et al., Journal of General Virology 67, 1199-1203) with a monoclonal antibody specific to the F protein or the HN protein did not reveal any F protein produced by the recombinant. The F protein produced by infection of CEFs with NDV was detected by the monoclonal antibody, but at a lower level than the HN, and so if the same ratio of native to recombinant protein held for the F as for the HN, the recombinant F might indeed not be seen.

G. Protection of Birds Against NDV Challenge 14 day old Rhode Island Red chickens were inoculated intravenously with $10^6$ pfu/bird of the F gene recombinant (4 birds) or of a fowlpox strain FP9 having no inserted genes (6 birds). 6 birds were left uninoculated. The 10 birds not inoculated with the recombinant are hereinafter referred to as 'the control birds'. At 28 days the inoculation was repeated. At 64 days the birds were challenged intramuscularly with $10^5 \times ELD_{50}$ (ELD=embryo lethal dose) of the virulent Herts 33 strain of NDV. At 3 days after challenge, 4 of the control birds were dead and 8 were very sick. At 4 days after challenge, 10 out of 12 control birds were dead, and by 5 days after challenge all the control birds were dead. All 4 birds inoculated with the F recombinant were normal.

Serum was taken from birds inoculated with the F recombinant and control birds before challenge with NDV. Examination of this serum by probing Western blots of purified NDV virions, showed that only the serum from the birds inoculated with the F recombinant had antibodies to the F protein. Thus although it was not possible to detect F protein produced by the recombinant in vitro, the in vivo experiment showed very convincingly that protection could be achieved, and that F protein in some form has been produced by the FPV recombinant containing the NDV F gene.

Example 6 describes a protection experiment using the NDV HN gene constructs of this Example.

EXAMPLE 4

This Example demonstrates vaccination of birds at one day of age with an NDV F gene/ FPV recombinant.

Groups of six or seven Rhode Island Red chicks were inoculated, at one day of age, by the wing-web method with either the NDV F gene/poxine FPV recombinant described in Example 3 or the Px4.1 parent poxine FPV strain. Each virus strain was inoculated into four groups of birds, at doses of $5 \times 10^4$, $5 \times 10^3$, $5 \times 10^2$, and $5 \times 10^1$ pfu/bird. Thus there were eight groups in all, with an additional group of uninoculated birds. Birds were inoculated at one day of age and challenged intramuscularly 26 days later, as in Application 8907374. Table 1 shows the results of this challenge. Uninoculated and control birds were not protected against challenge, all 38 birds being dead by 4 days. The birds inoculated with the fowlpox/NDV F recombinant were protected to a significant degree, 22 birds out of 28 surviving the challenge (79%). The dose of vaccine used appeared to have little effect on the levels of protection, although the lowest dose gave the best protection.

TABLE 1

| Inoculum | Viral dose- | Total number of birds dead at days 3-6 after challenge with NDV Herts 33 strain: days 3 | day 4 | day 5 | day 6 |
|---|---|---|---|---|---|
| NDV F gene/ | $5 \times 10^4$ | 0/7 | 0/7 | 2/7 | 2/7 |
| P × 4.1 FPV | $5 \times 10^3$ | 0/7 | 0/7 | 2/7 | 2/7 |
| recombinant | $5 \times 10^2$ | 1/7 | 1/7 | 2/7 | 2/7 |
| | $5 \times 10$ | 0/7 | 0/7 | 0/7 | 0/7 |
| P × 4.1 FPV alone | $5 \times 10^4$ | 6/7 | 7/7 | | |
| | $5 \times 10^3$ | 3/6 | 6/6 | | |
| | $5 \times 10^2$ | 5/6 | 6/6 | | |
| | $5 \times 10$ | 1/5 | 5/5 | | |
| Uninoculated | — | 4/7 | 7/7 | | |

EXAMPLE 5

This Example confirms the results given in Example 3 (Section G) for vaccination of birds with an NDV F gene recombinant and shows that it can be done by using the wing web as well as the intravenous route.

The procedure of Example 3 was followed, except that the booster inoculation was at 27 days from birth (rather than 28) and the challenge at 42 days from birth (rather than 64), the parent poxine strain was used as control, and there were five groups of birds (two inoculated iv, two wing web and one uninoculated).

The results in Table 2 show that all the birds inoculated with the NDV F gene/poxine FPV recombinant survived, whereas all the others died.

TABLE 2

| Inoculum | Method | Total number of birds dead at days 3, 4 and 14 after challenge with NDV Herts 33 strain: day 3 | day 4 | day 14 |
|---|---|---|---|---|
| NDV F gene/ P × 4.1 FPV | | | | |
| recombinant | iv | 0/6 | 0/6 | 0/6 |
| P × 4.1 FPV alone | iv | 6/6 | | |
| NDV F gene/ P × 4.1 FPV | | | | |
| recombinant | wing-web | 0/6 | 0/6 | 0/6 |
| P × 4.1 FPV alone | wing-web | 4/6 | 6/6 | |
| Uninoculated | — | 9/13 | 13/13 | |

EXAMPLE 6

This Example shows that a NDV HN gene/FPV recombinant also gives protection. Thus, protection can be obtained from either the F or the HN gene alone.

Example 5 was repeated except that the NDV HN/HP 440 FPV recombinant as described in Example 3 (Section E) was used with the HP 440 strain as control.

Table 3 shows the results. Again, the NDV NH gene-vaccinated birds were protected while the others all died.

TABLE 3

| Inoculum | Method | Total number of birds dead at days 3, 4 and 14 after challenge with NDV Herts 33 strain: day 3 | day 4 | day 14 |
|---|---|---|---|---|
| NDV HN gene/ HP 440 FPV | | | | |
| recombinant | iv | 1/6 | 1/6 | 1/6 |
| HP 440 alone | iv | 6/6 | | |
| Uninoculated | — | 9/13 | 13/13 | |

EXAMPLE 7

In this Example recombination vectors were made using the Egogpt gene, the constructs being of a generally similar kind to those described by CSIRO in the already cited PCT Application WO 88/02022, but flanked by non-essential region sequences of the present invention rather than TK gene sequences. The recombination vectors comprise in order:

(1) Non-essential region (around the Bgl III site)
(2) Ecogpt gene
(3) VV P.5 promoter
(4) VV P11 promoter
(5) IBV spike protein gene
(6) Non-essential region.

Note that the two promoters are "back-to-back", as shown in WO 88/02022, transcribing in opposite direction.

The clone pEFL2 (containing the vaccinia P7.5 promoter and beta-galactosidase gene in the FPV terminal fragment, see above) was cut with the restriction enzymes SphI and NcoI, repaired as described, and religated. The resulting construct, designated pEFL18, had lost approximately 850 base pairs of FPV sequence, as expected, but had also lost a HindIII site immediately adjacent to the SphI site. Thus, this plasmid contains only two HindIII sites, very close together, between the P7.5 promoter and the beta-galactosidase gene. (Digestion with HindIII thus only removes a very small fragment and can be used for the insertion of gene fragments containing their own ATG codon to make beta-galactosidase fusion constructs). This plasmid was cut with HindIII and EspI (EspI cuts near to the 3' end of the beta-galactosidase gene) and repaired. Into this repaired site was inserted a BglII/ApaI fragment (repaired) from the plasmid PSV2gpt (Mulligan & Berg, Science 209, 422-1427, 1980) which contained the *E.coli* ecogpt gene. Thus, the beta-galactosidase gene was removed and the Ecogpt gene was placed under the control of the P7.5 promoter. A unique SalI site upstream of the promoter allows insertion of other promoters or promoter/gene constructs. This plasmid was called pEFGP13.

The P11 late vaccinia promoter was excised from pMM6 (a gift from Michael Mackett) provided with multiple cloning sites (BamHI, XhoI, XbaI and SalI) by transfer to pUC19 and the resultant P1-cloning site construct inserted into the SalI site of pEFGPT3. The resultant plasmid was designated pEFGPT6 and allows insertion of genes at various sites under the control of the P11 promoter. An Infectious Bronchitis Virus spike protein gene (see NRDC's PCT Application publication No. WO86/05806) was inserted downstream of the promoter.

The plasmid pEFGPT3 was allowed to recombine into FPV strain FP9, as described above. Recombinant viruses were selected by the use of MXHAT medium containing myc ophenolic acid (Boyle & Coupar, Gene 65, 123-129, 1988). After the initial recombination in the presence of MXHAT medium, the virus was released by freeze-thawing and passaged twice under selective conditions. A cytopathic effect was seen, indicating that virus was growing under the selective conditions. Virus was then plaqued out and probed with an Ecogpt-specific probe. A high proportion of plaques (approximately 75%) were positive, indicating that the selection had been successful (normally only 0.1% of the virus would be recombinants) and hence that recombinants expressing the Ecogpt gene had been isolated.

Similar recombination experiments were carried out to incorporate the Ecogpt gene into the Poxine strain of FPV. After the recombination and upon passage in selective conditions, a cytopathic effect of the virus could be seen, indicating that recombinant virus expressing the Ecogpt gene had been produced. This confirms that the BglII non-essential region (as well as the SpaI region) is present in Poxine.

We claim:

1. A recombinant fowlpox virus (FPV) which contains within the long unique sequence of the terminal inverted repeat of the fowlpox virus genome, at least one foreign gene and at least one sequence for regulating the expression of the or each foreign gene.

2. A cloning vector containing a fowlpox non-essential region (NER) sequence being interrupted by at least one foreign gene and at least one sequence for regulating the expression of the foreign gene, said NER sequence being homologously recombinable with sequence within the long unique sequence (LUS) of the terminal inverted repeat (TIR) of the fowlpox virus genome.

3. A DNA molecule which consists essentially of a fowlpox non-essential region (NER) sequence being interrupted by at least one foreign gene and at least one sequence for regulating the expression of the foreign gene, said NER sequence being homologously recombinable with sequence within the long unique sequence (LUS) of the terminal inverted repeat (TIR) of the fowlpox virus genome.

4. A recombination vector comprising a cloning vector, said cloning vector containing a fowlpox non-essential region (NER) sequence being interrupted by at least one foreign gene and at least one sequence for regulating the expression of a said foreign gene, said NER sequence being homologously recombinable with sequence within the long unique sequence (LUS) of the terminal inverted repeat (TIR) of the fowlpox virus genome.

5. A recombination vector according to claim 4 wherein the NER sequence is homologously recombinable with sequence within 2.2 Kilobase pairs from the external end of the LUS.

6. A recombination vector according to claim 5 wherein the NER sequence is homologously recombinable with sequence within an open-reading frame (ORF) which is substantially one of those at 4125-4790, 5261-5629 or 5883-6185 of the nucleic acid sequence as shown in FIG. 15 or a variant thereof occurring in another strain of FPV.

7. A recombination vector according to claim 4, 5 or 6, which comprises in order:

(1) a first homologously recombinable flanking sequence,
(2) a first portion of said NER sequence,
(3) promoter DNA,
(4) a foreign gene transcribably downstream of the promoter whereby when the fowlpox virus RNA polymerase binds to the promoter it will transcribe the foreign gene into mRNA,
(5) a second portion of said NER sequence, the first and second portions being in the same relative orientation as are the first and second portions of the non-essential region within the viral genome and (6) a second homologously recombinable flanking sequence.

8. A recombinant fowlpox virus (FPV) which is the product of homologous recombination of a parent FPV with a recombination vector claimed in claim 4, 5, or 6.

9. An in vitro culture of animal cells infected with a recombinant FPV according to claim 8 or 1.

10. A culture according to claim 9, wherein the animal is a chicken.

* * * * *